US 7,326,779 B2

(12) United States Patent
Nakano et al.

(10) Patent No.: US 7,326,779 B2
(45) Date of Patent: Feb. 5, 2008

(54) PRIMERS AND METHOD OF DETECTING BACTERIA

(75) Inventors: Shigeru Nakano, Osaka (JP); Toru Kobayashi, Osaka (JP); Kenichi Funabiki, Osaka (JP); Yasuhiro Nagao, Osaka (JP); Toshihiro Yamada, Osaka (JP)

(73) Assignee: Nissin Food Products Co., Ltd., Osaka-Shi (JP)

( * ) Notice: Subject to any disclaimer, the term of this patent is extended or adjusted under 35 U.S.C. 154(b) by 365 days.

(21) Appl. No.: 10/491,449

(22) PCT Filed: Oct. 11, 2002

(86) PCT No.: PCT/JP02/10573

§ 371 (c)(1),
(2), (4) Date: Apr. 14, 2004

(87) PCT Pub. No.: WO03/033694

PCT Pub. Date: Apr. 24, 2003

(65) Prior Publication Data

US 2005/0176001 A1    Aug. 11, 2005

(30) Foreign Application Priority Data

Oct. 15, 2001    (JP)    ............... 2001-317341

(51) Int. Cl.
*C07H 21/04*    (2006.01)
*C12Q 1/68*    (2006.01)
*C12P 19/34*    (2006.01)

(52) U.S. Cl. ............... 536/23.1; 536/24.3; 435/6; 435/91.2

(58) Field of Classification Search ............... None
See application file for complete search history.

(56) References Cited

U.S. PATENT DOCUMENTS 6,030,818 A * 2/2000 Page et al. ............ 435/123
6,677,153 B2 * 1/2004 Iversen ............ 435/375

FOREIGN PATENT DOCUMENTS

| JP | 5-227998 | 9/1993 |
|---|---|---|
| JP | 2001-149073 | 6/2001 |
| WO | WO01/20032 | 3/2001 |

OTHER PUBLICATIONS

Greisen et al., PCR primers and probes for the 16S rRNA gene of most species of pathogenic bacteria, including bacteria found in cerebrospinal fluid. J. Clin. Microbiol. (1994) 32: 335-351.*
Buck et al., Design strategies and performance of custom DNA sequencing primers. BioTechniques (1999) 27: 528-536.*
Product #1256, Random Primer 24, New England Biolabs Catalog (1998-1999) p. 121.*
Product #1255, Random Primer 12, New England Biolabs Catalog (1998-1999) p. 121.*
K. Chen et al.; "Broad-range DNA probes for detecting and amplifying eubacterial nucleic acids"; FEMS Microbiol. Lett.; vol. 57; No. 1; 1989; pp. 19-24./Cited in the International Search Report.
J.J. Lu et al.; Use of PCR with universal primers and restriction endonuclease digestions for detection and identification of common bacterial pathogens in cerebrospinal fluid; J. Clin. Microbiol.; vol. 38; No. 6; Jun. 2000; pp. 2076-2080./Cited in the International Search Report./Discussed in the specification.
Ken'ichi Funabiki et al.; "Tokutei Saikingun no Jinsoku Kensaho no Kento (Dai 2 Ho)—Kenshutsuyo Primer no Tokuisei—"; *Japanese Society of Food Chemistry Dai 8 Kai Sokai•Gakujutsu Taikai Koen Yoshishu*, Jun. 21, 2002; p. 50./Cited in the International Search Report.
Toru Kobayashi et al.; "Tokutei Saikingun no Jinsoku Kensaho no Kento (Dai 3 Ho)—Kakushu Kako Shokuhin eno Tekiyo—"; *Japanese Society of Food Chemistry Dai 8 Kai Sokai•Gakujutsu Taikai Koen Yoshishu*, Jun. 21, 2002; p. 51./Cited in the International Search Report.
R.F. Wang et al.; "A universal protocol for PCR detection of 13 species of foodborne pathogens in foods."; J. Appl. Microbiol.; vol. 83; No. 6; Dec. 1997; pp. 727-736./Cited in the International Search Report./Discussed in the specification.
K. Chen et al.; "Broad-range DNA probes for detecting and amplifying eubacterial nucleic acids"; FEMS Microbiol. Lett.; vol. 57; No. 1; 1989; pp. 19-24./Cited in the International Search Report.
J.J. Lu et al.; Use of PCR with universal primers and restriction endonuclease digestions for detection and identification of common bacterial pathogens in cerebrospinal fluid; J. Clin Microbiol.; vol. 38; No. 6; Jun. 2000; pp. 2076-2080./Cited in the International Search Report./Discussed in the specification.
Ken'ichi Funabiki et al.; "Tokutei Saikingun no Jinsoku Kensaho no Kento (Dai 2 Ho)—Kenshutsuyo Primer no Tokuisei—"; *Japanese Society of Food Chemistry Dai 8 Kai Sokai•Gakujutsu Taikai Koen Yoshishu*, Jun. 21, 2002; p. 50./Cited in the International Search Report.

(Continued)

*Primary Examiner*—Young J. Kim
*Assistant Examiner*—David C. Thomas
(74) *Attorney, Agent, or Firm*—Kratz, Quintos & Hanson, LLP (57) ABSTRACT

The first primer of the invention is a primer which, when used in PCR under appropriate conditions, serves to detectably amplify 16S rRNA-encoding DNAs of bacteria of the *Escherichia*, *Salmonella* and *Vibrio* genera, but when used in PCR under the same conditions, does not serve to detectably amplify either chloroplast 16S rRNA-encoding DNAs or mitochondrial 16S rRNA-encoding DNAs. The second primer of the invention is a primer which, when used in PCR under appropriate conditions, serves to detectably amplify 16S rRNA-encoding DNAs of *Staphylococcus aureus* and *Bacillus cereus*, but when used in PCR under the same conditions, does not serve to detectably amplify either chloroplast 16S rRNA-encoding DNAs or mitochondrial 16S rRNA-encoding DNAs.

8 Claims, 3 Drawing Sheets

OTHER PUBLICATIONS

Toru Kobayashi et al.; "Tokutei Saikingun no Jinsoku Kensaho no Kento (Dai 3 Ho)—Kakushu Kako Shokuhin eno Tekiyo—"; *Japanese Society of Food Chemistry Dai 8 Kai Sokai•Gakujutsu Taikai Koen Yoshishu*, Jun. 21, 2002; p. 51./Cited in the International Search Report.

R.F. Wang et al.; "A universal protocol for PCR detection of 13 species of food-borne pathogens in foods."; *J. Appl. Microbiol.*; vol. 83; No. 6; Dec. 1997; pp. 727-437./Cited in the International Search Report./Discussed in the specification.

Klausegger et al; "Gram Type-Specific Broad-Range PCR Amplification for Rapid Detection of 62 Pathogenic Bacteria"; J. Clin. Microbiology (Feb. 1999), pp. 464-466.

Rupf et al; "Quanitification of Bacteria in Oral Samples by Competitive Polymerase Chain Reation"; J. Dent. Res. (Apr. 1999); 78(4); pp. 850-856.

International Search Report dated Dec. 24, 2002.

XP-002345101; Sleigh et al; "Detection of bacteraemia in critically ill patients using 16s rDNA polymerase chain reaction and DNA sequencing;" Intensive Care Med (2001); 27:1269-1273.

XP-001159737; Lantz et al; "Detection of pathogenic *Yersinia enterocolitica* in enrichment media and port by a multiplex PCR: a study sample preparation and PCR-inhibitory components;" Int. J.Food Micro.; (1998) 45: 93-105.

XP-002345102; Ovreas et al; "Distribution of Bacterioplankton in Meromictic Lake Saelenvannet, as Determined by Denaturing Gradient Gel Electophoresis of PCR-Amplified Gene Fragments Coding for 16S r RNA;" App. Envir. Microbiology; (Sep. 1997); vol. 63, No. 9, pp. 3367-3373.

XP-009053974; Nakano et al; "PCR Detection of *Bacillus* and *Staphylococcus* in Various Foods;" J. Food Protection; (2004) vol. 67, No. 6; pp. 1271-1277.

XP-002345300; Nakano et al; "Development of PCR assay for detection of *Enterobacteriaceae* in foods;" J. Food Protection (Oct. 2003); vol. 66:10; pp. 1798-1804—Abstract.

European Search Report dated Oct. 6, 2005.

* cited by examiner

Fig. 1

Number of copies of DNA as subjected to PCR

M: Molecular weight markers

① 0　② 10　③ $10^2$　④ $10^3$ (A), (B): Set of primers of SEQ ID NOs:1 and 2

(C), (D): Set of primers of SEQ ID NOs:3 and 4

Fig. 2

Number of copies of DNA as subjected to PCR

M: Molecular weight markers

①1  ②10  ③$10^2$  ④$10^3$ a upper section: Set of primers of SEQ ID NOs:1 and 2 b middle section: Set of primers of SEQ ID NOs:3 and 4 c lower section: Set of primers of J. Dent. Res.

(A) Wheat flour, (B) potato, (C) soybean, (D) corn

Fig. 3

Cell count per ml of ground noodle liquid

(A) *Escherichia coli*

(B) *Bacillus cereus*

Cultivation time (hours)

① 0  ② 5  ③ 6  ④ 7  ⑤ 18

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
gttgtaaagc actttcagtg gtgaggaagg                                  30

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
gcctcaaggg cacaacctcc aag                                         23

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
cttgctcctc tgaagttagc ggcg                                        24

<210> SEQ ID NO 4
<211> LENGTH: 33
<212> TYPE: DNA
<213> ORGANISM: Artificial Sequence
<220> FEATURE:
<223> OTHER INFORMATION: Synthetic

<400> SEQUENCE: 4
tgttcttccc taataacaga gttttacgac ccg                              33
```

PRIMERS AND METHOD OF DETECTING BACTERIA

TECHNICAL FIELD

The present invention relates to PCR primers for detecting bacteria belonging to *Escherichia*, *Salmonella*, and *Vibrio* genera. The invention also relates to PCR primers for detecting bacteria belonging to *Staphylococcus* and *Bacillus* genera, in particular PCR primers for detecting *Staphylococcus aureus* and *Bacillus cereus*. Further, the invention relates to a method for detecting bacteria in foodstuffs using these primers.

BACKGROUND ART

In the prior art, to check the presence or absence of specific bacteria, such as foodborne pathogenic bacteria in foodstuff, bacteria are isolated from foodstuffs and cultured, and visual observation of the colonies (for color reactions and morphology of the colonies), microscopic observation, Gram-staining, biochemical testing and other tests are made. These methods require at least 2 days to demonstrate the presence or absence of the specific bacteria. Such methods can hardly be employed on manufacture s voluntary inspection of foodstuffs prior to shipment thereof since even though it can successfully detect bacteria, the resulting delay in taking due measures is intolerable.

In recent years, methods have been developed which comprise isolating bacteria from foodstuffs and culturing the same, and testing the thus-obtained colonies by the PCR method (Science, 230, 1350 (1985)) using primers corresponding to DNA of specific bacterial species to rapidly detect the specific bacterial DNA (Japanese Unexamined Patent Publications 1999-332600, 1995-236500, and 1993-317098). However, even when these methods are used, these methods require at least one day for isolation of bacteria from foodstuffs and cultivation of them.

DNAs coding for rRNAs (ribosomal ribonucleic acids) are often used as the targets for detection by the PCR method. This is because rRNAs exist in all organisms except for viruses and show high levels of homology among organisms of the same species because of relatively slow rates of evolution thereof. As regards bacterial 16S rRNA, in particular, numerous sequence data has been accumulated, therefore, DNAs encoding 16S rRNA seems to suit for detecting bacteria by the PCR method.

It has also been proposed that a direct PCR assay with broad-range PCR primers capable of hybridizing with many bacterial 16S rRNA-encoding DNAs are used for detecting a large variety of bacteria by use of bacterial DNA extracted from test samples (J. Dent. Res. 78(4): 850-856 (1999); J. Clinical Microbiology June 2000, 2076-2080; J. Clinical Microbiology February 1999, 464-466).

However, in cases where foodstuffs are used as test materials, the DNAs of the foodstuffs themselves are also extracted by the procedure for extracting bacterial DNAs. Therefore, if the primers are low in specificity, those chloroplast or mitochondrial DNAs derived from the foodstuffs, too, will be amplified, making the presence or absence of bacteria ambiguous.

To overcome such disadvantages, it is also possible to use primers capable of specifically hybridizing with the DNAs coding for the 16S rRNA of specific bacterial species (J. Applied Microbiology 1997, 83, 727-736). In this case, however, it becomes necessary to carry out tests separately for individual target bacterial species, hence the number of tests per foodstuff sample would increase. Thus, this method could hardly be employed by foodstuff manufacturers in voluntary testing.

DISCLOSURE OF THE INVENTION

It is an object of the present invention to provide PCR primers with which the presence or absence of a plurality or group of specific bacterial species, containing foodborne pathogenic bacteria causative, in foodstuffs can be detected easily and rapidly, and a method by which the presence or absence of specific bacteria and a specific group of bacteria in foodstuffs can be easily and rapidly detected using those primers.

The present inventors made investigations in an attempt to accomplish the above object and made the following findings i) to iv).

i) When a DNA extraction procedure is carried out with a foodstuff and, with the DNA mixture obtained, the PCR method is carried out using primers capable of hybridizing with DNAs coding for 16S rRNAs of plurality of bacterial species (such a DNA being hereinafter referred to as 16S r-DNA), the possibility of the plant chloroplast 16S r-DNAs being simultaneously detected is high since bacterial 16S r-DNAs and plant chloroplast 16S r-DNAs are similar to each other in sequence.

Therefore, for avoiding the simultaneous detection of foodstuff-derived 16S r-DNAs in the PCR method applied to DNAs extracted from foodstuffs, it is necessary to use primers serving to amplify the 16S r-DNAs of the target bacterial species but not serving to amplify chloroplast 16S r-DNAs.

ii) Those main problem-bacteria possibly existing in foodstuffs and causing food poisoning include a group of bacteria which consist of bacteria of *Escherichia* (including O-157 and other pathogenic *Escherichia coli* stains) and *Salmonella* genera belonging to the Enterobacteriaceae family; bacteria of the *Vibrio* genus belonging to the Vibrioaceae family; bacteria of the *Staphylococcus* (including *Staphylococcus aureus*) and *Bacillus* (including *Bacillus cereus*) genera. Therefore, the presence or absence of those main problem bacteria in foodstuffs can be checked in a simple and easy manner by carrying out the PCR procedure using primers serving to amplify DNAs of bacteria of *Escherichia*, *Salmonella* and *Vibrio* genera and the PCR procedure using primers serving to amplify DNAs of bacteria of the *Staphylococcus* (in particular *Staphylococcus aureus*) and *Bacillus* (in particular *Bacillus cereus*) genera.

iii) Further, when the primers serving to amplify the 16S r-DNAs of bacteria of the *Escherichia*, *Salmonella* and *Vibrio* genera do not serve to amplify the 16S r-DNAs of bacteria other than the group of bacteria consisting of bacteria of the Enterobacteriaceae and Vibrioaceae families, the possibility of false-positive reactions can be reduced. As a result, the sensitivity of detection of the targeted bacteria can be improved. Similarly, when the primers serving to amplify the 16S r-DNAs of bacteria of the *Staphylococcus* (in particular *Staphylococcus aureus*) and *Bacillus* (in particular *Bacillus cereus*) genera do not serve to amplify the 16S r-DNAs of bacteria other than the group of bacteria consisting of bacteria of the Staphylococcaceae and Bacillaceae families, the possibility of false-positive reactions can be reduced. As a result, the sensitivity of detection of the targeted bacteria can be improved.

iv) Contaminants contained in foodstuffs may inhibit the PCR procedure in certain instances. Therefore, when the step mentioned below, for instance, is carried out after grinding the foodstuff sample, the bacteria contained in the foodstuff sample can be efficiently separated from the foodstuff sample.

When the ground foodstuff sample is centrifuged at a relatively low speed, namely by a centrifugal force of about 50 to 300×g, the insoluble ingredient and the cell debris in the foodstuff sample mostly precipitate while bacteria remain in the supernatant; thus bacteria can be separated from the foodstuff sample. The bacteria can be harvested by centrifuging the supernatant by a centrifugal force of 2,000×g or greater.

Therefore, when DNA is extracted from the bacteria-containing sediment obtained by such a centrifugation procedure and the PCR is carried out using the DNA obtained as template, simultaneous detection of DNA originating from the food can be avoided more effectively and, further, the influence of PCR-inhibiting contaminants possibly contained in foodstuffs can be avoided.

Investigations based on such findings as described above have now led to completion of the present invention, which provides the following primers, primer sets, PCR kit, and method for detecting bacteria.

1. A primer which, when used in PCR under appropriate conditions, serves to detectably amplify 16S rRNA-encoding DNAs of bacteria of the *Escherichia, Salmonella* and *Vibrio* genera, but when used in PCR under the same conditions, does not serve to detectably amplify either chloroplast 16S rRNA-encoding DNAs or mitochondrial 16S rRNA-encoding DNAs.

2. A primer according to Item 1 which, when used in PCR under the above conditions, may serve to detect the group of bacteria of the Enterobacteriaceae and Vibrioaceae families.

3. A primer according to Item 1 or 2 which, when used in PCR under appropriate conditions, serves to detectably amplify 16S rRNA-encoding DNAs of bacteria of the *Escherichia, Salmonella* and *Vibrio* genera, but when used in PCR under the same conditions, does not serve to detectably amplify 16S rRNA-encoding DNAs of bacteria other than the group of bacteria of the Enterobacteriaceae and Vibrioaceae families.

4. A primer which, when used in PCR under appropriate conditions, serves to detectably amplify 16S rRNA-encoding DNAs of *Staphylococcus aureus* and *Bacillus cereus,* but when used in PCR under the same conditions, does not serve to detectably amplify either chloroplast 16S rRNA-encoding DNAs or mitochondrial 16S rRNA-encoding DNAs.

5. A primer according to Item 4 which, when used in PCR under the above conditions, may serve to detect the group of bacteria consisting of bacteria of the Staphylococcaceae, Bacillaceae and Aerococcaceae families.

6. A primer according to Item 4 or 5 which, when used in PCR under appropriate conditions, serves to detectably amplify 16S rRNA-encoding DNAs of *Staphylococcus aureus* and *Bacillus cereus,* but when used in PCR under the same conditions, does not serve to detectably amplify 16S rRNA-encoding DNAs of bacteria other than the group of bacteria consisting of bacteria of the Staphylococcaceae, Bacillaceae and Aerococcaceae families.

7. A primer which, when used in PCR under appropriate conditions, serves to detectably amplify 16S rRNA-encoding DNAs of bacteria of the *Staphylococcus* and *Bacillus* genera, but when used in PCR under the same conditions, does not serve to detectably amplify either chloroplast 16S rRNA-encoding DNAs or mitochondrial 16S rRNA-encoding DNAs.

8. A primer according to Item 7 which, when used in PCR under the above conditions, may serve to detect the group of bacteria of bacteria of the Staphylococcaceae, Bacillaceae and Aerococcaceae families.

9. A primer according to Item 7 or 8 which, when used in PCR under the above conditions, serves to detectably amplify 16S rRNA-encoding DNAs of bacteria of the *Staphylococcus* and *Bacillus* genera, but when used in PCR under the same conditions, does not serve to detectably amplify 16S rRNA-encoding DNAs of bacteria other than the group of bacteria consisting of bacteria of the Staphylococcaceae, Bacillaceae and Aerococcaceae families.

10. The following primer (1) or (2):
    (1) A primer consisting of the base sequence of base numbers 21 to 30, the base sequence of base numbers 20 to 30, the base sequence of base numbers 19 to 30, the base sequence of base numbers 18 to 30, the base sequence of base numbers 17 to 30, the base sequence of base numbers 16 to 30, the base sequence of base numbers 15 to 30, the base sequence of base numbers 14 to 30, the base sequence of base numbers 13 to 30, the base sequence of base numbers 12 to 30, the base sequence of base numbers 11 to 30, the base sequence of base numbers 10 to 30, the base sequence of base numbers 9 to 30, the base sequence of base numbers 8 to 30, the base sequence of base numbers 7 to 30, the base sequence of base numbers 6 to 30, the base sequence of base numbers 5 to 30, the base sequence of base numbers 4 to 30, the base sequence of base numbers 3 to 30, the base sequence of base numbers 2 to 30 or the base sequence of base numbers 1 to 30 in SEQ ID NO:1;
    (2) A primer which is a DNA comprising at most 40 bases and containing, on the 3 terminal side thereof, the base sequence of base numbers 21 to 30, the base sequence of base numbers 20 to 30, the base sequence of base numbers 19 to 30, the base sequence of base numbers 18 to 30, the base sequence of base numbers 17 to 30, the base sequence of base numbers 16 to 30, the base sequence of base numbers 15 to 30, the base sequence of base numbers 14 to 30, the base sequence of base numbers 13 to 30, the base sequence of base numbers 12 to 30, the base sequence of base numbers 11 to 30, the base sequence of base numbers 10 to 30, the base sequence of base numbers 9 to 30, the base sequence of base numbers 8 to 30, the base sequence of base numbers 7 to 30, the base sequence of base numbers 6 to 30, the base sequence of base numbers 5 to 30, the base sequence of base numbers 4 to 30, the base sequence of base numbers 3 to 30, the base sequence of base numbers 2 to 30,or the base sequence of base numbers 1 to 30 in SEQ ID NO:1.

11. The following primer (3) or (4):
    (3) A primer consisting of the base sequence of base numbers 14 to 23, the base sequence of base numbers 13 to 23, the base sequence of base numbers 12 to 23, the base sequence of base numbers 11 to 23, the base sequence of base numbers 10 to 23, the base sequence of base numbers 9 to 23, the base sequence of base numbers 8 to 23, the base sequence of base numbers 7 to 23, the base sequence of base numbers 6 to 23, the base sequence of base numbers 5 to 23, the base sequence of base numbers 4 to 23, the base sequence of base numbers 3 to 23, the base sequence of base numbers 2 to 23 or the base sequence of base numbers 1 to 23 in SEQ ID NO:2;

(4) A primer which is a DNA comprising at most 40 bases and containing, on the 3 terminal side thereof, the base sequence of base numbers 14 to 23, the base sequence of base numbers 13 to 23, the base sequence of base numbers 12 to 23, the base sequence of base numbers 11 to 23, the base sequence of base numbers 10 to 23, the base sequence of base numbers 9 to 23, the base sequence of base numbers 8 to 23, the base sequence of base numbers 7 to 23, the base sequence of base numbers 6 to 23, the base sequence of base numbers 5 to 23, the base sequence of base numbers 4 to 23, the base sequence of base numbers 3 to 23, the base sequence of base numbers 2 to 23 or the base sequence of base numbers 1 to 23 in SEQ ID NO:2.

12. The following primer (5) or (6):

(5) A primer consisting of the base sequence of base numbers 15 to 24, the base sequence of base numbers 14 to 24, the base sequence of base numbers 13 to 24, the base sequence of base numbers 12 to 24, the base sequence of base numbers 11 to 24, the base sequence of base numbers 10 to 24, the base sequence of base numbers 9 to 24, the base sequence of base numbers 8 to 24, the base sequence of base numbers 7 to 24, the base sequence of base numbers 6 to 24, the base sequence of base numbers 5 to 24, the base sequence of base numbers 4 to 24, the base sequence of base numbers 3 to 24, the base sequence of base numbers 2 to 24 or the base sequence of base numbers 1 to 24 in SEQ ID NO:3;

(6) A primer which is a DNA comprising at most 40 bases and containing, on the 3 terminal side thereof, the base sequence of base numbers 15 to 24, the base sequence of base numbers 14 to 24, the base sequence of base numbers 13 to 24, the base sequence of base numbers 12 to 24, the base sequence of base numbers 11 to 24, the base sequence of base numbers 10 to 24, the base sequence of base numbers 9 to 24, the base sequence of base numbers 8 to 24, the base sequence of base numbers 7 to 24, the base sequence of base numbers 6 to 24, the base sequence of base numbers 5 to 24, the base sequence of base numbers 4 to 24, the base sequence of base numbers 3 to 24, the base sequence of base numbers 2 to 24 or the base sequence of base numbers 1 to 24 in SEQ ID NO:3.

13. The following primer (7) or (8):

(7) A primer consisting of the base sequence of base numbers 24 to 33, the base sequence of base numbers 23 to 33, the base sequence of base numbers 22 to 33, the base sequence of base numbers 21 to 33, the base sequence of base numbers 20 to 33, the base sequence of base numbers 19 to 33, the base sequence of base numbers 18 to 33, the base sequence of base numbers 17 to 33, the base sequence of base numbers 16 to 33, the base sequence of base numbers 15 to 33, the base sequence of base numbers 14 to 33, the base sequence of base numbers 13 to 33, the base sequence of base numbers 12 to 33, the base sequence of base numbers 11 to 33, the base sequence of base numbers 10 to 33, the base sequence of base numbers 9 to 33, the base sequence of base numbers 8 to 33, the base sequence of base numbers 7 to 33, the base sequence of base numbers 6 to 33, the base sequence of base numbers 5 to 33, the base sequence of base numbers 4 to 33, the base sequence of base numbers 3 to 33, the base sequence of base numbers 2 to 33 or the base sequence of base numbers 1 to 33 in SEQ ID NO:4;

(8) A primer which is a DNA comprising at most 40 bases and containing, on the 3 terminal side thereof, the base sequence of base numbers 24 to 33, the base sequence of base numbers 23 to 33, the base sequence of base numbers 22 to 33, the base sequence of base numbers 21 to 33, the base sequence of base numbers 20 to 33, the base sequence of base numbers 19 to 33, the base sequence of base numbers 18 to 33, the base sequence of base numbers 17 to 33, the base sequence of base numbers 16 to 33, the base sequence of base numbers 15 to 33, the base sequence of base numbers 14 to 33, the base sequence of base numbers 13 to 33, the base sequence of base numbers 12 to 33, the base sequence of base numbers 11 to 33, the base sequence of base numbers 10 to 33, the base sequence of base numbers 9 to 33, the base sequence of base numbers 8 to 33, the base sequence of base numbers 7 to 33, the base sequence of base numbers 6 to 33, the base sequence of base numbers 5 to 33, the base sequence of base numbers 4 to 33, the base sequence of base numbers 3 to 33, the base sequence of base numbers 2 to 33 or the base sequence of base numbers 1 to 33 in SEQ ID NO:4.

14. A primer set comprising a primer according to Item 10 and a primer according to Item 11.

15. A primer set comprising a primer according to Item 12 and a primer according to Item 13.

16. A PCR kit comprising a primer set according to Item 14 and a primer set according to Item 15.

17. A method for detecting bacteria which comprises the step i) of extracting DNAs contained in a foodstuff sample to be tested therefrom and the step ii) of carrying out the PCR using a primer according to any of Items 1 to 13 with the DNA extracted as template and detecting the DNA thus amplified.

18. A method for detecting bacteria which comprises the step i) of extracting DNAs contained in a foodstuff sample to be tested therefrom and the step ii) of carrying out the PCR using a primer set according to Item 14 or 15 with the DNA extracted as template and detecting the DNA thus amplified.

19. A method for detecting bacteria according to Item 17 or 18, wherein the DNA extracting step i) comprises the step a) of grinding the foodstuff sample to be tested, the step b) of centrifuging the ground sample by a centrifugal force of 50 to 300×g, the step c) of centrifuging the supernatant obtained by centrifugation in step b) by a centrifugal force of 2000 to 14,000×g and the step d) of extracting DNAs contained in the sediment obtained by centrifugation in step c) therefrom.

20. A primer which, when used in PCR under appropriate conditions, serves to detectably amplify 16S rRNA-encoding DNAs of bacteria of the Enterobacteriaceae and Vibrioaceae families, but when used in PCR under the same conditions, does not serve to detectably amplify either chloroplast 16S rRNA-encoding DNAs or mitochondrial 16S rRNA-encoding DNAs.

21. A primer which, when used in PCR under appropriate conditions, serves to detectably amplify 16S rRNA-encoding DNAs of bacteria of the Staphylococcaceae and Bacillaceae families, but when used in PCR under the same conditions, does not serve to detectably amplify either chloroplast 16S rRNA-encoding DNAs or mitochondrial 16S rRNA-encoding DNAs.

DETAILED DESCRIPTION OF THE INVENTION (I) Primers (I-I) Basic Constitution of Primers The first primer of the invention is a primer which, when used in PCR under appropriate conditions, serves to detectably amplify 16S r-DNAs of bacteria of the *Escherichia, Salmonella* and *Vibrio* genera, but does not serve to detectably amplify either chloroplast 16S r-DNAs or mitochondrial 16S r-DNAs, when used in PCR under the same conditions.

The second primer of the invention is a primer which, when used in PCR under appropriate conditions, serves to detectably amplify 16S r-DNAs of *Staphylococcus aureus* and *Bacillus cereus*, but when used in PCR under the same conditions, does not serve to detectably amplify either chloroplast 16S r-DNAs or mitochondrial 16S r-DNAs.

The appropriate conditions mentioned above include those conditions generally employed in PCR procedures, for example, the denaturation carried out at about 90-98° C. for about 3 seconds to 1 minute, the annealing at about 50-65° C. for about 5 seconds to 2 minutes, the DNA elongation at about 60-75° C. for about 10 seconds to 3 minutes, and about 1-3.5 mM of the Mg ion concentration.

When used in PCR under appropriate conditions, the first primer of the invention serves to detectably amplify 16S r-DNAs of bacteria of the *Escherichia, Salmonella* and *Vibrio* genera and may serve to detectably amplify 16S r-DNAs of bacteria of the Enterobacteriaceae and Vibrioaceae families. It is preferable that, under the same conditions, the above primer does not serve to detectably amplify any of the DNAs derived from bacteria not belonging to the Enterobacteriaceae or Vibrioaceae family, algae, fungi, protist, etc. It is preferable that the above primer does not serve to detectably amplify 16S r-DNAs of bacteria not belonging to the Enterobacteriaceae or Vibrioaceae family, in particular. Thus, preferably, the first primer of the invention, when used in PCR under appropriate conditions, serves to detectably amplify 16S r-DNAs of bacteria of the *Escherichia, Salmonella* and *Vibrio* genera, but when used in PCR under the same conditions, does not serve to detectably amplify 16S r-DNAs of bacteria other than the group of bacteria consisting of bacteria of the Enterobacteriaceae and Vibrioaceae families. By saying that the primer does not serve to detectably amplify 16S r-DNAs of bacteria other than the group of bacteria consisting of bacteria of the Enterobacteriaceae and Vibrioaceae families, it is not only meant that none of those other bacteria is detected but also meant that cases where one to several other bacterial species are exceptionally detected are included.

The bacteria of the family Enterobacteriaceae include bacteria of the *Escherichia, Salmonella, Shigella, Citrobacter, Klebsiella, Enterobacter, Erwinia, Serratia, Hafnia, Edwardsiella, Yersinia, Providencia* genera, etc. The bacteria of the family Vibrioaceae include bacteria of the *Vibrio, Photobacterium, Listonella* genera, etc. In this invention, bacteria of the genus *Aeromonas* are included in bacteria of the Vibrioaceae family.

The bacteria other than the group of bacteria consisting of bacteria of the Enterobacteriaceae and Vibrioaceae families are not particularly restricted.

The second primer of the invention, when used in PCR under appropriate conditions, serves to detect 16S r-DNAs of *Staphylococcus aureus* and *Bacillus cereus* and may serve to detectably amplify 16S r-DNAs of bacteria of the Staphylococcaceae and Bacillaceae families. Preferably, the second primer of the invention serves to detect 16S r-DNAs of bacteria of the *Staphylococcus* and *Bacillus* genera.

Preferably, the second primer of the invention does not serve to detectably amplify any of the DNAs derived from bacteria other than the group of bacteria consisting of bacteria of the Staphylococcaceae, Bacillaceae and Aerococcaceae families, algae, fungi, protist and so forth under the same conditions. Preferably, in particular, it does not serve to detectably amplify 16S r-DNAs of bacteria other than the group of bacteria consisting of bacteria of the Staphylococcaceae, Bacillaceae and Aerococcaceae families. Thus, preferably, the second primer of the invention serves to detectably amplify 16S r-DNAs of *Staphylococcus aureus* and *Bacillus cereus* when used in PCR under appropriate conditions, but when used in PCR under the same conditions, does not serve to detectably amplify 16S r-DNAs of bacteria other than the group of bacteria consisting of bacteria of the Staphylococcaceae, Bacillaceae and Aerococcaceae families. By saying that the above primer does not serve to detectably amplify 16S r-DNAs of bacteria other than the group of bacteria consisting of bacteria of the Staphylococcaceae, Bacillaceae and Aerococcaceae families, it is not only meant that none of those other bacteria is detected but also meant that cases where one to several other bacterial species are exceptionally detected are included.

The bacteria of the family Staphylococcaceae include bacteria of the *Staphylococcus* genus. The bacteria of the *Staphylococcus* genus include such species as *Staphylococcus aureus, Staphylococcus epidermidis, Staphylococcus xylosus,* and *Staphylococcus succinus*. The bacteria of the Bacillaceae family include bacteria of the *Bacillus* genus. The bacteria of the *Bacillus* genus include *Bacillus cereus, Bacillus thuringiensis, Bacillus licheniformis, Bacillus megaterium, Bacillus pumilus, Bacillus subtilis,* etc. The bacteria of the Aerococcaceae family include bacteria of the *Aerococcus* genus. The bacteria of the *Aerococcus* genus include *Aerococcus viridans, Aerococcus urinae,* etc.

The bacteria other than the group of bacteria consisting of bacteria of the Staphylococcaceae, Bacillaceae and Aerococcaceae families are not particularly restricted.

(I-II) Significance of the Primers of the Invention

The reason why the first primer of the invention is intended for detecting bacteria of the *Escherichia, Salmonella* and *Vibrio* genera and the second primer of the invention is intended for detecting bacteria of the *Staphylococcus* (in particular *Staphylococcus aureus*) and *Bacillus* (in particular *Bacillus cereus*) genera is as follows.

Thus, bacteria of the *Escherichia* genus are bacteria regarded as an indicator of oral contamination, and the possibility of the main species thereof, namely *Escherichia coli*, being widely found in foodstuffs is high. Recently, highly lethal strains, such as the pathogenic *Escherichia coli* O-157, have also been found. Bacteria of the *Salmonella* genus are mostly found in eggs, fishes and shellfishes and, in Japan, they are food poisoning causing bacteria most frequently reported. Bacteria of the *Vibrio* genus are detected in marine fishes and shellfishes. Further, *Staphylococcus aureus* belonging to the *Staphylococcus* genus is widely detected in foodstuffs as a result of staining or contamination of fingers and so forth. Further, *Bacillus cereus* belonging to the *Bacillus* genus is relatively often detected in rice and noodle products. Thus, bacteria of the *Escherichia, Salmonella,* and *Vibrio* genera, *Staphylococcus aureus* and *Bacillus cereus* are the important food poisoning causing bacteria reported in Japan.

Further, in some countries, testing for *Escherichia coli*, bacteria of the *Salmonella* and *Vibrio* genera and *Staphylococcus aureus* is legally obligatory. *Bacillus cereus* is a bacterial species for which testing is conducted voluntarily by many foodstuff manufacturers.

(I-III) Target Foodstuffs

The foodstuffs which are the targets of the PCR using the primer(s) of the present invention are not particularly restricted but widely include, among others, noodle products, meats, fishes, shellfishes, vegetables, cereals, dairy products, and products resulting from processing of these.

(I-IV) Specific Examples of the First Primer

The base sequence of the primer of the invention for detecting bacteria includes base sequences complementary to the base sequence of the DNA to be detected, and base sequences derived from such complementary base sequences by deletion, insertion or substitution of about 1 to 5 bases.

The base sequence of the primer of the invention for detecting bacteria further includes the base sequences described in the present specification, base sequences derived therefrom by deletion, insertion or substitution of about 1 to 5 bases, and base sequences complementary thereto.

Typically, the first primer of the invention may be the following primer A) or B).

A) The following primer (1) or (2):

(1) A primer comprising the base sequence of base numbers 21 to 30, the base sequence of base numbers 20 to 30, the base sequence of base numbers 19 to 30, the base sequence of base numbers 18 to 30, the base sequence of base numbers 17 to 30, the base sequence of base numbers 16 to 30, the base sequence of base numbers 15 to 30, the base sequence of base numbers 14 to 30, the base sequence of base numbers 13 to 30, the base sequence of base numbers 12 to 30, the base sequence of base numbers 11 to 30, the base sequence of base numbers 10 to 30, the base sequence of base numbers 9 to 30, the base sequence of base numbers 8 to 30, the base sequence of base numbers 7 to 30, the base sequence of base numbers 6 to 30, the base sequence of base numbers 5 to 30, the base sequence of base numbers 4 to 30, the base sequence of base numbers 3 to 30, the base sequence of base numbers 2 to 30 or the base sequence of base numbers 1 to 30 in the sequence identification number 1 (SEQ ID-NO:1);

(2) A primer which is a DNA comprising at most 40 bases and containing, on the 3 terminal side thereof, the base sequence of base numbers 21 to 30, the base sequence of base numbers 20 to 30, the base sequence of base numbers 19 to 30, the base sequence of base numbers 18 to 30, the base sequence of base numbers 17 to 30, the base sequence of base numbers 16 to 30, the base sequence of base numbers 15 to 30, the base sequence of base numbers 14 to 30, the base sequence of base numbers 13 to 30, the base sequence of base numbers 12 to 30, the base sequence of base numbers 11 to 30, the base sequence of base numbers 10 to 30, the base sequence of base numbers 9 to 30, the base sequence of base numbers 8 to 30, the base sequence of base numbers 7 to 30, the base sequence of base numbers 6 to 30, the base sequence of base numbers 5 to 30, the base sequence of base numbers 4 to 30, the base sequence of base numbers 3 to 30, the base sequence of base numbers 2 to 30 or the base sequence of base numbers 1 to 30 in SEQ ID NO:1.

Thus, the primer A) is a DNA having any of the base sequences in SEQ ID NO:1 as enumerated above or a DNA having a length of at most 40 bases as a whole and resulting from addition of an arbitrary base sequence to the 5 terminal side of any of the base sequences enumerated above.

Preferred among them is a primer consisting of the base sequence of base numbers 16 to 30, the base sequence of base numbers 15 to 30, the base sequence of base numbers 14 to 30, the base sequence of base numbers 13 to 30, the base sequence of base numbers 12 to 30, the base sequence of base numbers 11 to 30, the base sequence of base numbers 10 to 30, the base sequence of base numbers 9 to 30, the base sequence of base numbers 8 to 30, the base sequence of base numbers 7 to 30, the base sequence of base numbers 6 to 30, the base sequence of base numbers 5 to 30, the base sequence of base numbers 4 to 30, the base sequence of base numbers 3 to 30, the base sequence of base numbers 2 to 30 or the base sequence of base numbers 1 to 30 in SEQ ID NO:1, or a primer which is a DNA comprising at most 40 bases and containing any of these base sequences on the 3 terminal side thereof.

More preferred is a primer consisting of the base sequence of base numbers 11 to 30, the base sequence of base numbers 10 to 30, the base sequence of base numbers 9 to 30, the base sequence of base numbers 8 to 30, the base sequence of base numbers 7 to 30, the base sequence of base numbers 6 to 30, the base sequence of base numbers 5 to 30, the base sequence of base numbers 4 to 30, the base sequence of base numbers 3 to 30, the base sequence of base numbers 2 to 30 or the base sequence of base numbers 1 to 30 in SEQ ID NO:1, or a primer which is a DNA comprising at most 40 bases and containing any of these base sequences on the 3 terminal side thereof.

Still more preferred is a primer consisting of the base sequence of base numbers 6 to 30, the base sequence of base numbers 5 to 30, the base sequence of base numbers 4 to 30, the base sequence of base numbers 3 to 30, the base sequence of base numbers 2 to 30 or the base sequence of base numbers 1 to 30 in SEQ ID NO:1, or a primer which is a DNA comprising at most 40 bases and containing any of these base sequences on the 3 terminal side thereof.

Most preferred is the primer consisting of the base sequence of base numbers 1 to 30 in SEQ ID NO:1, or a primer which is a DNA comprising at most 40 bases and containing this base sequence on the 3 terminal side thereof.

B) The following primer (3) or (4):

(3) A primer consisting of the base sequence of base numbers 14 to 23, the base sequence of base numbers 13 to 23, the base sequence of base numbers 12 to 23, the base sequence of base numbers 11 to 23, the base sequence of base numbers 10 to 23, the base sequence of base numbers 9 to 23, the base sequence of base numbers 8 to 23, the base sequence of base numbers 7 to 23, the base sequence of base numbers 6 to 23, the base sequence of base numbers 5 to 23, the base sequence of base numbers 4 to 23, the base sequence of base numbers 3 to 23, the base sequence of base numbers 2 to 23 or the base sequence of base numbers 1 to 23 in SEQ ID NO:2;

(4) A primer which is a DNA comprising at most 40 bases and containing, on the 3 terminal side thereof, the base sequence of base numbers 14 to 23, the base sequence of base numbers 13 to 23, the base sequence of base numbers 12 to 23, the base sequence of base numbers 11 to 23, the base sequence of base numbers 10 to 23, the base sequence of base numbers 9 to 23, the base sequence of base numbers 8 to 23, the base sequence of base numbers 7 to 23, the base sequence of base numbers 6 to 23, the base sequence of base numbers 5 to 23, the base sequence of base numbers 4 to 23, the base sequence of base numbers 3 to 23, the base sequence of base numbers 2 to 23 or the base sequence of base numbers 1 to 23 in SEQ ID NO:2.

Thus, the primer B) is a DNA having any of the base sequences in SEQ ID NO:2 as enumerated above or a DNA having a length of at most 40 bases as a whole and resulting from addition of an arbitrary base sequence to the 5 terminal side of any of the base sequences enumerated above.

Preferred among them is a primer consisting of the base sequence of base numbers 9 to 23, the base sequence of base numbers 8 to 23, the base sequence of base numbers 7 to 23, the base sequence of base numbers 6 to 23, the base sequence of base numbers 5 to 23, the base sequence of base numbers 4 to 23, the base sequence of base numbers 3 to 23, the base sequence of base numbers 2 to 23 or the base sequence of base numbers 1 to 23 in SEQ ID NO:2, or a primer which is a DNA comprising at most 40 bases and containing any of these base sequences on the 3 terminal side thereof.

More preferred is a primer consisting of the base sequence of base numbers 4 to 23, the base sequence of base numbers 3 to 23, the base sequence of base numbers 2 to 23 or the base sequence of base numbers 1 to 23 in SEQ ID NO:2, or a primer which is a DNA comprising at most 40 bases and containing any of these base sequences on the 3 terminal side thereof. Most preferred is the primer consisting of the base sequence of bases 1 to 23 in SEQ ID NO:2, or a primer which is a DNA comprising at most 40 bases and containing this base sequence on the 3 terminal side thereof.

In the primers A) and B), the base sequence optionally added on the 5 terminal side preferably comprises about 1 to 10 bases, in particular about 1 to 5 bases. Most preferably, however, no addition is made of such optional base sequence.

(I-V) Specific Examples of the Second Primer

Typically, the second primer of the invention may be the following primer C) or D).

C) The following primer (5) or (6):
(5) A primer consisting of the base sequence of base numbers 15 to 24, the base sequence of base numbers 14 to 24, the base sequence of base numbers 13 to 24, the base sequence of base numbers 12 to 24, the base sequence of base numbers 11 to 24, the base sequence of base numbers 10 to 24, the base sequence of base numbers 9 to 24, the base sequence of base numbers 8 to 24, the base sequence of base numbers 7 to 24, the base sequence of base numbers 6 to 24, the base sequence of base numbers 5 to 24, the base sequence of base numbers 4 to 24, the base sequence of base numbers 3 to 24, the base sequence of base numbers 2 to 24 or the base sequence of base numbers 1 to 24 in SEQ ID NO:3;
(6) A primer which is DNA comprising at most 40 bases and containing, on the 3 terminal side thereof, the base sequence of base numbers 15 to 24, the base sequence of base numbers 14 to 24, the base sequence of base numbers 13 to 24, the base sequence of base numbers 12 to 24, the base sequence of base numbers 11 to 24, the base sequence of base numbers 10 to 24, the base sequence of base numbers 9 to 24, the base sequence of base numbers 8 to 24, the base sequence of base numbers 7 to 24, the base sequence of base numbers 6 to 24, the base sequence of base numbers 5 to 24, the base sequence of base numbers 4 to 24, the base sequence of base numbers 3 to 24, the base sequence of base numbers 2 to 24 or the base sequence of base numbers 1 to 24 in SEQ ID NO:3.

Thus, the primer C) is a DNA having any of the base sequences in SEQ ID NO:3 as enumerated above or a DNA having a length of at most 40 bases as a whole and resulting from addition of an arbitrary base sequence to the 5 terminal side of any of the base sequences enumerated above.

Preferred among them is a primer comprising the base sequence of base numbers 10 to 24, the base sequence of base numbers 9 to 24, the base sequence of base numbers 8 to 24, the base sequence of base numbers 7 to 24, the base sequence of base numbers 6 to 24, the base sequence of base numbers 5 to 24, the base sequence of base numbers 4 to 24, the base sequence of base numbers 3 to 24, the base sequence of base numbers 2 to 24 or the base sequence of base numbers 1 to 24 in SEQ ID NO:3, or a primer which is a DNA comprising at most 40 bases and containing any of these base sequences on the 3 terminal side thereof.

More preferred is a primer consisting of the base sequence of base numbers 5 to 24, the base sequence of base numbers 4 to 24, the base sequence of base numbers 3 to 24, the base sequence of base numbers 2 to 24 or the base sequence of base numbers 1 to 24 in SEQ ID NO:3, or a primer which is a DNA comprising at most 40 bases and containing any of these base sequences on the 3 terminal side thereof.

Most preferred is the primer consisting of the base sequence of base numbers 1 to 24 in SEQ ID NO:3, or a primer which is a DNA comprising at most 40 bases and containing this base sequence on the 3 terminal side thereof.

D) The following primer (7) or (8):
(7) A primer consisting of the base sequence of base numbers 24 to 33, the base sequence of base numbers 23 to 33, the base sequence of base numbers 22 to 33, the base sequence of base numbers 21 to 33, the base sequence of base numbers 20 to 33, the base sequence of base numbers 19 to 33, the base sequence of base numbers 18 to 33, the base sequence of base numbers 17 to 33, the base sequence of base numbers 16 to 33, the base sequence of base numbers 15 to 33, the base sequence of base numbers 14 to 33, the base sequence of base numbers 13 to 33, the base sequence of base numbers 12 to 33, the base sequence of base numbers 11 to 33, the base sequence of base numbers 10 to 33, the base sequence of base numbers 9 to 33, the base sequence of base numbers 8 to 33, the base sequence of base numbers 7 to 33, the base sequence of base numbers 6 to 33, the base sequence of base numbers 5 to 33, the base sequence of base numbers 4 to 33, the base sequence of base numbers 3 to 33, the base sequence of base numbers 2 to 33 or the base sequence of base numbers 1 to 33 in SEQ ID NO:4;
(8) A primer which is a DNA comprising at most 40 bases and containing, on the 3 terminal side thereof, the base sequence of base numbers 24 to 33, the base sequence of base numbers 23 to 33, the base sequence of base numbers 22 to 33, the base sequence of base numbers 21 to 33, the base sequence of base numbers 20 to 33, the base sequence of base numbers 19 to 33, the base sequence of base numbers 18 to 33, the base sequence of base numbers 17 to 33, the base sequence of base numbers 16 to 33, the base sequence of base numbers 15 to 33, the base sequence of base numbers 14 to 33, the base sequence of base numbers 13 to 33, the base sequence of base numbers 12 to 33, the base sequence of base numbers 11 to 33, the base sequence of base numbers 10 to 33, the base sequence of base numbers 9 to 33, the base sequence of base numbers 8 to 33, the base sequence of base numbers 7 to 33, the base sequence of base numbers 6 to 33, the base sequence of base numbers 5 to 33, the base sequence of base numbers 4 to 33, the base sequence of base numbers 3 to 33, the base sequence of base numbers 2 to 33 or the base sequence of base numbers 1 to 33 in SEQ ID NO:4.

Thus, the primer D) is a DNA having any of the base sequences in SEQ ID NO:4 as enumerated above or a DNA having a length of at most 40 bases as a whole and resulting from addition of an arbitrary base sequence to the 5 terminal side of any of the base sequences enumerated above.

Preferred among them is a primer consisting of the base sequence of base numbers 19 to 33, the base sequence of base numbers 18 to 33, the base sequence of base numbers 17 to 33, the base sequence of base numbers 16 to 33, the base sequence of base numbers 15 to 33, the base sequence of base numbers 14 to 33, the base sequence of base numbers 13 to 33, the base sequence of base numbers 12 to 33, the base sequence of base numbers 11 to 33, the base sequence of base numbers 10 to 33, the base sequence of base numbers 9 to 33, the base sequence of base numbers 8 to 33, the base sequence of base numbers 7 to 33, the base sequence of base numbers 6 to 33, the base sequence of base numbers 5 to 33, the base sequence of base numbers 4 to 33, the base sequence of base numbers 3 to 33, the base sequence of base numbers 2 to 33 or the base sequence of base numbers 1 to 33 in SEQ ID NO:4, or a primer which is a DNA comprising at most 40 bases and containing any of these base sequences on the 3 terminal side thereof.

More preferred is a primer consisting of the base sequence of base numbers 14 to 33, the base sequence of base numbers 13 to 33, the base sequence of base numbers 12 to 33, the base sequence of base numbers 11 to 33, the base sequence of base numbers 10 to 33, the base sequence of base numbers 9 to 33, the base sequence of base numbers 8 to 33, the base sequence of base numbers 7 to 33, the base sequence of base numbers 6 to 33, the base sequence of base numbers 5 to 33, the base sequence of base numbers 4 to 33, the base sequence of base numbers 3 to 33, the base sequence of base numbers 2 to 33 or the base sequence of base numbers 1 to 33 in SEQ ID NO:4, or a primer which is a DNA comprising at most 40 bases and containing any of these base sequences on the 3 terminal side thereof.

Still more preferred is a primer consisting of the base sequence of base numbers 9 to 33, the base sequence of base numbers 8 to 33, the base sequence of base numbers 7 to 33, the base sequence of base numbers 6 to 33, the base sequence of base numbers 5 to 33, the base sequence of base numbers 4 to 33, the base sequence of base numbers 3 to 33, the base sequence of base numbers 2 to 33 or the base sequence of base numbers 1 to 33 in SEQ ID NO:4, or a primer which is a DNA comprising at most 40 bases and containing any of these base sequences on the 3 terminal side thereof.

Most preferred is the primer consisting of the base sequence of base numbers 1 to 33 in SEQ ID NO:4, or a primer which is a DNA comprising at most 40 bases and containing this base sequence on the 3 terminal side thereof.

In the primers C) and D), the base sequence optionally added on the 5 terminal side preferably comprises about 1 to 7 bases, in particular about 1 to 5 bases. Most preferably, however, no addition is made of such optional base sequence.

(I-VI) Method for Producing the Primers

The primers of the invention can be produced with ease by chemical synthesis.

(I-VII) Method for Using the Primers

The first primer of the invention can be used in PCR in combination with a known universal primer and capable of detecting eubacteria, or a set of two first primers of the invention can be used as a sense primer/antisense primer set. In particular, the use of a set of two first primers of the invention is preferred. Such use further increases the sensitivity in detecting the targeted bacterial group. For example, the primer A) or B) may be used in combination with a primer with which eubacteria can be detected, or the primer A) and primer B) may be used in combination as a primer set consisting of a sense primer and an antisense primer. The latter case is more preferred.

The first primer of the invention can be used in detecting bacteria of the *Escherichia, Salmonella* and *Vibrio* genera. It can be used in detecting bacteria of the Enterobacteriaceae and Vibrioaceae families as well.

Similarly, the second primer of the invention can be used in PCR in combination with an eubacteria-detectable primer known in the art, or a set of two second primers of the invention can be used as a sense primer/antisense primer set. In particular, the use of a set of two second primers of the invention is preferred. Such use further increases the sensitivity in detecting the targeted group of bacteria. For example, the primer C) or D) may be used in combination with a primer with which bacteria in general can be detected, or the primer C) and primer D) may be used in combination as a primer set consisting of a sense primer and an antisense primer. The latter case is more preferred.

The second primer of the invention can be used in detecting bacteria of the *Staphylococcus* (in particular *Staphylococcus aureus*) and *Bacillus* (in particular *Bacillus cereus*) genera.

Furthermore, the first primer set and second primer set of the invention can be used in combination as a PCR set. The PCR set of the invention can be used in detecting bacteria of the *Escherichia, Salmonella* and *Vibrio* genera (or bacteria of the Enterobacteriaceae and Vibrioaceae families) as well as bacteria of the *Staphylococcus* (in particular *Staphylococcus aureus*) and *Bacillus* (in particular *Bacillus cereus*) genera.

More specifically, for testing the presence or absence of a specific bacterial group in foodstuffs using the PCR set of the invention, the PCR using the first primer of the invention to detect bacteria of the *Escherichia, Salmonella* and *Vibrio* genera and the PCR using the second primer of the invention to detect bacteria of the *Staphylococcus* (in particular *Staphylococcus aureus*) and *Bacillus* (in particular *Bacillus cereus*) genera can be carried out separately. By carrying out these two PCRs simultaneously, it becomes possible to detect the specific targeted bacterial group by spending time and effort only once.

(II) Method for Detacting Bacteria

The method for detecting bacteria according to the invention comprises the step i) of extracting DNAs contained in a foodstuff sample to be tested therefrom and the step ii) of carrying out the PCR using the primer of the invention with the DNA extracted as template, followed by detecting the amplified-DNA.

(II-I) DNA Extraction Step

Target Foodstuffs

The foodstuffs as the targets of the method of the invention are not particularly restricted. The method of the invention can be applied to a wide variety of foodstuffs, including noodle products, meats, fishes, shellfishes, vegetables, cereals, dairy products, and products resulting from processing of these, and the like.

Outline of the DNA Extraction Step

In carrying out the method of the invention, the DNA may be extracted either from a culture of bacteria separated from a foodstuff, or directly from the foodstuff. It is also possible to extract the DNA from a fraction possibly containing bacteria after separation of the fraction possibly containing bacteria from the foodstuff by centrifugation of a foodstuff possibly containing bacteria. The last-mentioned method is most preferred as the step of DNA extraction from bacteria possibly contained in the foodstuff.

Preferred DNA Extraction Step

In the following, a preferred DNA extraction step is described in detail. Thus, in the method for detecting bacteria according to the invention, the DNA extracting step preferably comprises the step a) of grinding the foodstuff sample to be tested, the step b) of centrifuging the ground sample by a centrifugal force of about 50 to 300×g, the step c) of centrifuging the supernatant obtained by centrifugation in step b) by a centrifugal force of about 2000 to 14,000×g and the step d) of extracting the DNA contained in the pellets obtained by centrifugation in step c) therefrom. In the following, the respective steps are described in detail.

<Grinding Step>

The foodstuff sample can be ground in the usual manner by adding water or a buffer solution in an amount of about 5 to 20 times the weight of the foodstuff sample and grinding the foodstuff using a Stomacher® or like homogenizer. In the case of a liquid or semi-liquid foodstuff sample, if those samples are mixed and diluted with water or buffer solution, the grinding step may be omitted.

<Centrifugation Step>

Then, the ground foodstuff sample can be centrifuged generally at about 50 to 300×g, preferably at about 80 to 150×g, for about 1 to 2 minutes. This causes the ground foodstuff sample mostly to settle, while the bacteria remain in the supernatant. The supernatant is therefore collected.

The supernatant can be centrifuged generally at about 2,000 to 14,000×g, preferably at about 8,000 to 14,000×g, for about 2 to 5 minutes. Most of the bacteria can be precipitated from the supernatant by the centrifugation.

Then, to the precipitate is resuspended in water or a buffer solution in an amount of about 1/10 to 1/2 of the volume of the ground foodstuff liquid subjected to centrifugation treatment, and the resulting suspension containing bacteria can now be subjected to the DNA extraction step.

DNA Extraction Method

DNA extraction from the foodstuff sample or separated bacteria can be carried out employing any of the methods known in the art. Such known methods include the Marmur method, the enzyme method which is a modification of the Marmur method, the benzyl chloride method, and the like.

For confirming the presence or absence of specific bacteria including bacteria causing food poisoning prior to shipment of food products, it is necessary to rapidly extract the DNA. An example of the method of such rapid DNA extraction from bacteria is the Chelex method (Biotechniques, April 1991; 10(4):506-513; Microbiol. Res. May 1999; 154(1):23-26). The Chelex method comprises adding Chelex® solution in an amount of about 10% by weight to the bacterial suspension, heating on a boiling water bath for about 5 minutes for lysing the bacteria, centrifuging the bacterial lysate, and collecting the supernatant. The supernatant contains the DNA, and this DNA extract can be used in PCR.

As another example of the rapid DNA extraction method is the method comprising dissolving the bacterial pellets by adding about 10 to 30% by weight of sodium dodecyl sulfate, heating the mixture at about 60-100° C. for about 5-20 minutes for bacterial cell lysis, adding sodium chloride to the resulting solution to a salt concentration of 1 M, carrying out deproteinization, and subjecting the supernatant to ethanol precipitation for DNA preparation.

(II-II) Step of DNA Detection by PCR

In carrying out the PCR, the primers of the invention as described above are used. Generally, for one foodstuff sample, the PCR using the first primer of the invention for detecting bacteria of the *Escherichia, Salmonella* and *Vibrio* genera, and the PCR using the second primer of the invention for detecting bacteria of the *Staphylococcus* (in particular *Staphylococcus aureus*) and *Bacillus* (in particular *Bacillus cereus*) genera may be carried out.

More preferably, one set of the first primers of the invention are used as a sense primer and an antisense primer, and one set of the second primers of the invention are used as a sense primer and an antisense primer. The combined use of a primer A) and a primer B) and the combined use of a primer C) and a primer D) are particularly preferred.

The PCR conditions are not particularly restricted but optimal conditions may be selected for each PCR apparatus. For example, the following conditions may be used:

Thermal denaturation of double-stranded DNA to single-stranded DNA: Heating is generally made at about 90-98° C., preferably at about 92-96° C., generally for about 3 seconds to 1 minute, preferably for about 30 seconds to 1 minute.

Annealing: Heating is made generally at about 50-65° C., preferably at 50-60° C., generally for about 5 seconds to 2 minutes, preferably for about 30 seconds to 1 minute.

DNA elongation reaction: Heating is made generally at about 60-75° C., preferably at about 70-74° C., generally for about 10 seconds to 3 minutes, preferably for about 30 seconds to 2 minutes.

Mg ion concentration in the reaction liquid: Generally about 1-3.5 mM, preferably about 2-3 mM.

This reaction is carried out generally in about 20-40 cycles, preferably in about 30 cycles, whereby the target DNA can be amplified to a detectable level.

The PCR apparatus, for example, a commercial apparatus of the block type or capillary type can be used. For rapid DNA amplification, a capillary type PCR apparatus is preferably used.

The PCR product may further be subjected to separation by agarose gel electrophoresis, followed by nucleic acid staining with ethidium bromide or SYBR® Green, for instance.

A PCR amplification product DNA band in each PCR, when detected, indicates the existence of bacteria corresponding to the primer used.

When the PCR is carried out using the first primer and/or second primer of the invention and a band is detected in electrophoresis, the possibility is indicated of bacteria of the *Escherichia, Salmonella* and *Vibrio* genera existing in the test foodstuff. When the PCR is carried out using the primer having the base sequence of base numbers 1 to 30 in SEQ ID NO:1 and the primer having the base sequence of base numbers 1 to 23 in SEQ ID NO:2, a band corresponding to a DNA fragment of about 420 base pairs will generally be detected if bacteria of the *Escherichia, Salmonella* or *Vibrio* genus exist.

When the PCR is carried out using the third primer and/or fourth primer of the invention and a band is detected in electrophoresis, the possibility is indicated of the existence of bacteria of the *Staphylococcus* (in particular *Staphylococcus aureus*) and *Bacillus* (in particular *Bacillus cereus*) genera. When the PCR is carried out using the primer having the base sequence of base numbers 1 to 24 in SEQ ID NO:3 and the primer having the base sequence of base numbers 1 to 33 in SEQ ID NO:4, a band corresponding to a DNA fragment of about 380 base pairs will generally be detected if bacteria of the *Staphylococcus* genus including *Staphylococcus aureus* or bacteria of the *Bacillus* genus including *Bacillus cereus* are present.

It is also possible to carry out the analysis in a short time by using a real time PCR apparatus. In this case, the occurrence or nonoccurrence of a PCR amplification product can be confirmed by melting curve analysis following PCR. In cases where the judgment is difficult, such agarose gel electrophoresis as mentioned above may be carried out for the analysis.

In cases where a sufficient quantity of DNA cannot be obtained because of the number of bacterial cells obtained being excessively small or where the result of PCR is considered to be affected by dead bacterial cells, the number of bacterial cells can be increased by adding a sterilized liquid medium for bacterial culture to the test sample and by carrying out cultivation at about 30-37° C. In this way, the DNA detection sensitivity can be improved, and the influence of dead cells can be reduced. The liquid medium is not particularly restricted in type but may suitably be selected from a wide range of universal culture media for bacteria, such as brain heart infusion medium, Tryptosoya medium and the like. In the case of bacteria of the *Vibrio* genus, it is advisable that those media supplemented with about 1-3% sodium chrolide or an alkaline peptone medium are used.

When the foodstuff sample contains about 10 viable cells per gram thereof, about 4-8 hours of cultivation is generally sufficient for the DNA thereof to become detectable by the PCR described above. Such bacterial contamination that the number of bacteria to be detected (in particular bacteria of the *Escherichia* genus, *Salmonella* genus, *Staphylococcus aureus* or *Bacillus cereus*) in each gram of a foodstuff is less than 10 can be generally disregarded. This is because when the number of bacteria contained in each gram of a foodstuff is less than 10, smearing of a plate agar medium with the ground food liquid will not result in colony detection, hence such contamination is generally neglected. In cases where it is desired that the detectable number of bacteria per unit food weight be lowered, the sample size may be increased and/or the cultivation time may adequately be prolonged.

(III) Effects of the Invention

In accordance with the present invention, there are provided, PCR primers with which the presence or absence of a specific bacterial group, inclusive of food poisoning-causing bacteria, in foodstuffs can be detected easily and rapidly, and a method for easily and rapidly detecting the presence or absence of a specific bacterial group in foodstuffs using those primers.

In addition, when the primers of the invention are used, such DNAs as food-derived chloroplast DNA and mitochondrial DNA are not detected and, therefore, the PCR can be carried out without cultivation of bacteria following separation thereof from foodstuff samples. The time for testing can be shortened accordingly.

The crucial bacteria as food poisoning-causing bacteria in foodstuffs include bacteria of the genus *Escherichia*, bacteria of the *Salmonella*, *Vibrio*, *Staphylococcus* (in particular *Staphylococcus aureus*) and *Bacillus* (in particular *Bacillus cereus*) genera. Under such circumstances, the first primer of the invention can serve to detect a relatively broad range group of bacteria including bacteria of the *Escherichia*, *Salmonella* and *Vibrio* genera, while the second primer of the invention also can serve to detect a relatively broad range group of bacteria including *Staphylococcus aureus* and *Bacillus cereus* (including, in some instances, bacteria of the *Staphylococcus* and *Bacillus* genera). Therefore, when two PCR procedures using these two primers respectively are concurrently carried out, it is possible to expediently check the likelihood of contamination by main food poisoning causative bacteria.

Therefore, the primers of the invention can be preferably used in primary screening of bacterial testing of foodstuffs with a relatively low frequency of contamination. Thus, when no bacteria are detected in the primary screening using the primers of the invention, it is suggested that the above-mentioned group of bacteria detectable with those primers do not exist. When bacteria are detected in the primary screening using the primers of the invention, the bacterial species may be identified by carrying out the PCR, as a secondary screening, using primers specific to specific bacterial species.

When, in carrying out the method of the invention, the food grinding step and centrifugation procedure are carried out, bacteria can be efficiently separated and collected from foodstuff samples and, therefore, it is no more necessary to separate bacteria from foodstuff samples and cultivate the same, hence the testing time can be cut down accordingly.

EXAMPLES

The following examples illustrate the present invention more specifically. It is to be noted, however, that these examples are never restrictive of the scope of the present invention.

Example 1

Confirmation of Reactivity in Type Strains

<DNA Preparation>

Bacterial strains of *Escherichia coli* JCM $1649^T$, *Salmonella typhimurium* IFO 13245, *Staphylococcus aureus* IFO 3060 and *Bacillus cereus* IFO $15305^T$ were grown in brain heart infusion medium. Using DNeasy Tissue Kit (product of QIAGEN), DNA solutions were prepared from cells of the respective strains.

<Primer Preparation>

The DNA primers defined by SEQ ID NO:1, SEQ ID NO:2, SEQ ID NO:3 and SEQ ID NO:4 were synthesized using a DNA synthesizer.

<PCR>

The DNA amount in cells of each bacterial strain was determined, and test DNA solutions were prepared so that the genome copy number contained in the DNA solutions as estimated from the molecular weight of the genome of each bacterial strain might amount to about 10 copies/μl, about $10^2$ copies/μl or about $10^3$ copies/μl. Sterilized water and the buffer solution for PCR were added to 1 μl of each test DNA solution for adjustment to the following final concentrations: 2.0 mM $MgCl_2$, 50 mM Tris-HCl (pH 8.3), 0.25 mg/ml BSA, 200 μM dNTPs, 0.2 μM of each primer. Thereto was added 1.0 unit of Hot Start Taq DNA polymerase (product of Roche Diagnostics), and the PCR was carried out with a total liquid amount of 20 µl.

For *Escherichia coli* and *Salmonella typhimurium*, the primers of SEQ ID NO:1 and SEQ ID NO:2 were used in combination. For *Staphylococcus aureus* and *Bacillus cereus*, the primers of SEQ ID NO:3 and SEQ ID NO:4 were used in combination.

As for the temperature conditions for PCR, the reaction mixture was maintained at 95° C. for 15 minutes, then thermal denaturation was carried out at 95° C. for 5 seconds, annealing at 59° C. for 10 seconds and DNA elongation at 72° C. for 20 seconds. Under these conditions, the PCR was carried out in 30 cycles. The PCR apparatus used was LightCycler (product of Roche Diagnostics).

Each PCR product obtained was electrophoresed on 1.6% agarose gel (TaKaRa) at 100 V for 25 minutes using Mupid-2 (Cosmo Bio) and, after staining with ethidium bromide (1.0 µg/ml), band observation was made under a UV lamp.

Figure 1:
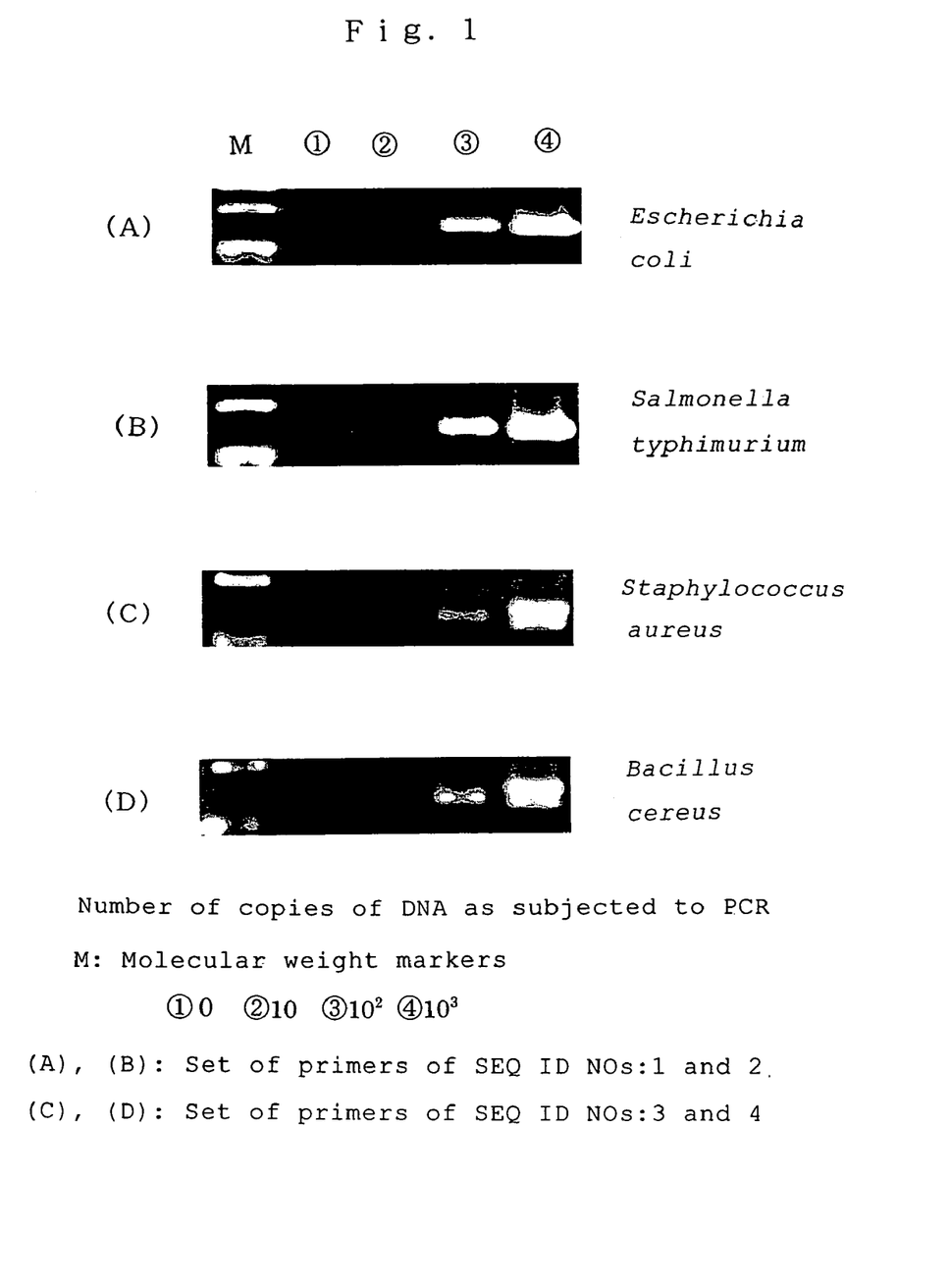
FIG. 1 is a representation of the agarose gel electrophoretic patterns after the PCR using the primers of the invention with type strain DNAs as templates.

The agarose gel electrophoretic patterns obtained are shown in FIG. 1. (A) and (B) in FIG. 1 are the results obtained by using the primers of SEQ ID NO:1 and SEQ ID NO:2 in combination, and (C) and (D) in FIG. 1 are the results obtained by using the primers of SEQ ID NO:3 and SEQ ID NO:4 in combination. (A) in FIG. 1 shows the result with *Escherichia coli*, (B) in FIG. 1 the result with *Salmonella typhimurium*, (C) in FIG. 1 the result with *Staphylococcus aureus*, and (D) in FIG. 1 the result with *Bacillus cereus*.

From FIG. 1, it was demonstrated that the DNAs of *Escherichia coli* and *Salmonella typhimurium* can be detected by the combined use of the primers of SEQ ID NO:1 and SEQ ID NO:2. It was also demonstrated that the DNAs of *Staphylococcus aureus* and *Bacillus cereus* can be detected by the combined use of the primers of SEQ ID NO:3 and SEQ ID NO:4. Further, it was confirmed that when such a genomic DNA exists in a quantity of about $10^2$ copies, the DNA can be detected under the above-specified PCR conditions.

Example 2

Reactivity with Plant DNAs

<DNA Preparation>

Respective plant DNAs were extracted from commercially available wheat flour, potato, soybean and corn using DNeasy Plant Mini Kit (product of Qiagen).

<PCR>

After determination of the DNA concentration in each plant DNA extract prepared, test DNA solutions corresponding in genomic DNA copy number in each solution to about $10^0$ copy/µl, about $10^1$ copies/µl, about $10^2$ copies/µl and about $10^3$ copies/µl as estimated from the molecular weight of DNA per genome in each plant species were prepared. Sterilized water and the buffer solution for PCR were added to 1 µl of each of these test DNA solutions for adjustment to the following final concentrations: 2.0 mM $MgCl_2$, 50 mM Tris-HCl (pH 8.3), 0.25 mg/ml BSA, 200 µM dNTPs, and 0.2 µM of each primer. Thereto was added 1.0 unit of Hot Start Taq DNA polymerase (product of Roche Diagnostics), and the PCR was carried out with a total liquid amount of 20 µl.

As for the primers, a set of the primer of SEQ ID No:1 and the primer of SEQ ID NO:2, a set of the primer of SEQ ID NO:3 and the primer of SEQ ID NO:4, and a primer set reported to serve to detect bacteria in general (J Dent Res 78(4):850-856, April, 1999) were used respectively.

As for the temperature conditions for PCR, the reaction mixture was maintained at 95° C. for 15 minutes, then thermal denaturation was carried out at 95° C. for 5 seconds, annealing at 59° C. for 10 seconds and DNA elongation at 72° C. for 20 seconds. Under these conditions, the PCR was carried out in 30 cycles. The PCR apparatus used was LightCycler (product of Roche Diagnostics).

Figure 2:
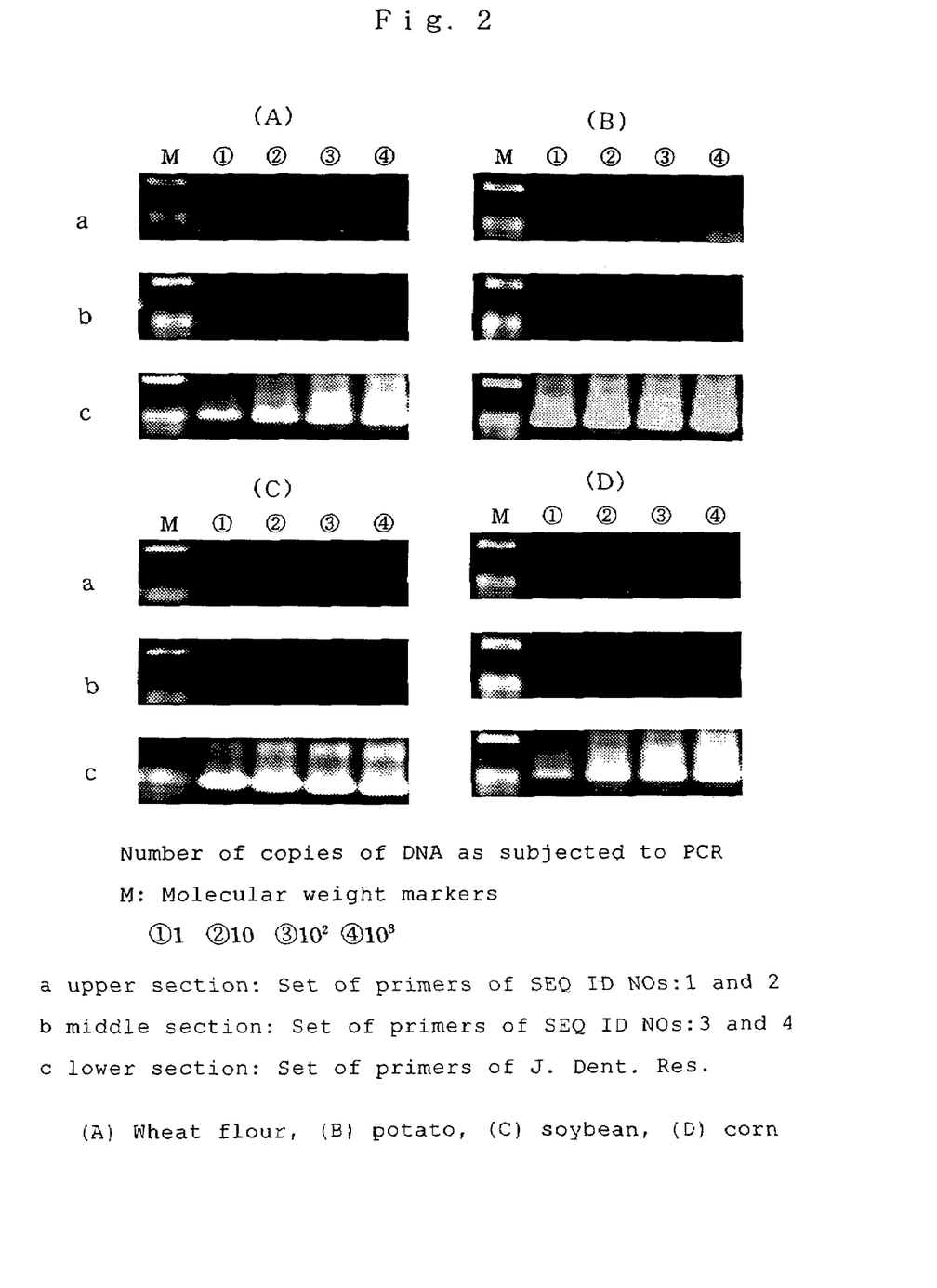
FIG. 2 is a representation of the agarose gel electrophoretic patterns after the PCR using the primers of the invention or the primers capable of detecting bacteria in general with plant-derived DNAs as templates.

Each PCR product obtained was electrophoresed on 1.6% agarose gel (TaKaRa) at 100 V for 25 minutes using Mupid-2 (Cosmo Bio). The gel obtained after electrophoresis was stained with ethidium bromide (1.0 µg/ml), and DNA band observation was made under a UV lamp. The results are shown in FIG. 2. (A) in FIG. 2 shows the result with wheat, (B) in FIG. 2 with potato, (C) in FIG. 2 with soybean, and (D) in FIG. 2 with corn.

As shown in FIG. 2, with all of wheat, potato, soybean and corn, no band was detected when the primers of SEQ ID NO:1 and SEQ ID NO:2 or the primers of SEQ ID NO:3 and SEQ ID NO:4 were used. It is thus evident that the PCR using the primers of the invention does not detect these plant-derived DNAs. On the other hand, the use of the above-mentioned primer set reported to be capable of detecting bacteria in general resulted in positive band detection. This is probably due to the reaction with plant-derived DNAs, including chloroplast or/and mitochondrial DNAs. The DNA base sequences of these amplification-due bands were examined and found to coincide with the chloroplast 16S rRNA genes of the respective plants.

Further, the same experiments were carried out using bovine DNA (product of GeneScan), chicken DNA (product of GeneScan), salmon DNA (product of Clontech), *Saccharomyces cerevisiae* IFO 0282 DNA and *Aspergillus oryzae* IFO 4206 DNA. It was confirmed that when the primers of SEQ ID NO:1 and SEQ ID NO:2 or the primers of SEQ ID NO:3 and SEQ ID NO:4 were used, no band was detected with any of the DNAS. It was thus found that those DNAs derived from mammals, birds, fishes and fungi are not detected by the PCR using the primers of the invention.

Example 3

Confirmation of Species Specificity of the Primers of the Invention

The bacterial strains listed below in Table 1 were cultured in the same manner as in Example 1 using media suited for the strains, and the DNA was extracted from the culture of each strain and subjected to PCR. The primers used were the primer of SEQ ID NO:1 in combination with the primer of SEQ ID NO:2, and the primer of SEQ ID NO:3 in combination with the primer of SEQ ID NO:4.

The results are shown in Table 1.

TABLE 1

| family | Genus, Species, and strains | Primers of SEQ ID Nos.: 1 and 2 | Primers of SEQ ID Nos.: 3 and 4 |
| --- | --- | --- | --- |
| Rhizobiaceae | *Agrobacterium radiobacter* ATCC 19358$^T$ | − | − |
| Alcaligenaceae | *Alcaligenes faecalis* JCM 1474$^T$ | − | − |
| Neisseriaceae | *Chromobacterium violaceum* JCM 1249$^T$ | − | − |
| | *Neisseria meningitides* ATCC 13077$^T$ | − | − |
| Xanthomonadaceae | *Xanthomonas maltophilia* JCM 1975$^T$ | − | − |
| Legionellaceae | *Legionella pneumophila* JCM 7571$^T$ | − | − |
| Pseudomonadaceae | *Pseudomonas aeruginosa* ATCC 27843$^T$ | − | − |
| | *Pseudomonas fluorescens* JCM 5963$^T$ | − | − |
| Moraxellaceae | *Moraxella antipestifer* JCM 9532$^T$ | − | − |
| | *Acinetobacter baumannii* JCM 6841$^T$ | − | − |
| Vibrionaceae | *Vibrio vulnificus* JCM 3725$^T$ | + | − |
| | *Vibrio parahaemolyticus* ATCC 17802$^T$ | + | − |
| | *Photobacterium leiognathi* ATCC 25521$^T$ | + | − |
| | *Aeromonas hydrophila* ATCC 7966$^T$ (1) | + | − |
| Enterobacteriaceae | *Enterobacter agglomerans* JCM 1236$^T$ | + | − |
| | *Enterobacter cloacae* JCM 1232$^T$ | + | − |
| | *Citrobacter freundii* JCM 1657$^T$ | + | − |
| | *Escherichia coli* JCM 1649$^T$ | + | − |
| | *Escherichia coli* JM109 | + | − |
| | *Escherichia coli* HB101 | + | − |
| | *Escherichia coli* 0157: H7 ATCC 43889 | + | − |
| | *Hafnia alvei* JCM 1666$^T$ | + | − |
| | *Klebsiella pneumoniae* JCM 1662$^T$ | + | − |
| | *Plesiomonas shigelloides* ATCC 14029$^T$ | + | − |
| | *Proteus mirabilis* JCM 1669$^T$ | − | − |
| | *Salmonella typhimurium* IFO 13245 | + | − |
| | *Salmonella typhimurium* IFO 14211 | + | − |
| | *Salmonella enteritidis* IFO 3313 | + | − |
| | *Serratia ficaria* JCM 1241$^T$ | + | − |
| | *Serratia marcescens* JCM 1239$^T$ | + | − |
| | *Shigella flexneri* ATCC 29903$^T$ | + | − |
| | *Yersina enterocolitica* ATCC 9610$^T$ | + | − |
| Pasteurellaceae | *Haemophilus influenzae* ATCC 33391$^T$ | − | − |
| Campylobacteraceae | *Campylobacter coli* ATCC 33559$^T$ | − | − |
| Helicobacteraceae | *Helicobacter pylori* ATCC 43504$^T$ | − | − |
| Clostridiaceae | *Clostridium perfringens* JCM 1290$^T$ | − | − |
| Eubacteriaceae | *Eubacterium alactolyticum* JCM 6480$^T$ (2) | − | − |
| Acidaminococcaceae | *Veillonella alcalescens* ATCC 27215 | − | − |
| Bacillaceae | *Bacillus cereus* IFO 15305$^T$ | − | + |
| | *Bacillus cereus* ATCC 11950 | − | + |
| | *Bacillus thuringiensis* ATCC 10792$^T$ | − | + |
| | *Bacillus licheniformis* JCM 2505$^T$ | − | + |
| | *Bacillus megaterium* JCM 2506$^T$ | − | + |
| | *Bacillus pumilus* JCM 2508$^T$ | − | + |
| | *Bacillus subtilis* IFO 13719$^T$ | − | + |
| Staphylococcaceae | *Staphylococcus aureus* IFO 3060 | − | + |
| | *Staphylococcus aureus* JCM 2874 | − | + |
| | *Staphylococcus epidermides* JCM 2414$^T$ | − | + |
| Lactobacillaceae | *Lactobacillus casei* JCM 1134$^T$ | − | − |
| | *Lactobacillus gasseri* JCM 1131$^T$ | − | − |
| | *Lactobacillus bulgaricus* JCM 1002$^T$ | − | − |
| Aerococcaceae | *Aerococcus viridans* IFO 12219$^T$ | − | + |
| Streptococcaceae | *Streptococcus mutans* JCM 5705$^T$ | − | − |
| | *Streptococcus salivarius* JCM 5707$^T$ | − | − |
| | *Streptococcus agalactiae* JCM 5671$^T$ | − | − |
| Coriobacteriaceae | *Collinsella aerofaciens* JCM 10188$^T$ | − | − |
| Actinomycetaceae | *Actinomyces naeslundii* JCM 8349$^T$ | − | − |
| Micrococcaceae | *Micrococcus luteus* JCM 1464$^T$ | − | − |
| Microbacteriaceae | *Microbacterium lacticum* JCM 1379 | − | − |
| Corynebacteriaceae | *Corynebacterium kutscheri* JCM 9385$^T$ | − | − |
| | *Corynebacterium xerosis* JCM 1971$^T$ | − | − |
| Propionibacteriaceae | *Propionibacterium acnes* JCM 6425$^T$ | − | − |
| Bifidobacteriaceae | *Bifidobacterium longum* JCM 1217$^T$ | − | − |
| | *Bifidobacterium adolescentis* JCM 1275$^T$ | − | − |
| Bacteroidaceae | *Bacteroides vulgatus* JCM 5826$^T$ | − | − |
| Porphyromonadaceae | *Porphyromonas gingivalis* ATCC 33277$^T$ | − | − |
| Prevotellaceae | *Prevotella intermedia* ATCC 25611$^T$ | − | − |
| Flavobacteriaceae | *Flavobacterium johnsoniae* JCM 8514$^T$ | − | − |

TABLE 1-continued

| family | Genus, Species, and strains | Primers of SEQ ID Nos.: 1 and 2 | Primers of SEQ ID Nos.: 3 and 4 |
|---|---|---|---|
| Flexibacteraceae | Cytophaga arvensicola JCM 2836$^T$ | − | − |
| Fusobacteriaceae | Fusobacterium nucleatum ATCC 25586$^T$ | − | − |

(1): The *Aeromonas* genus is currently belonged to the Vibrioaceae family. Recently, it has been proposed that it should be reclassified in the new Aeromodaceae family (TAXONOMIC OUTLINE OF THE *PROCARYOTE* GENERA, BERGEY S MANUAL OF SYSTEMATIC BACTERIOLOGY, SECOND EDITION Release 1.0, April 2001).
(2): The genus has been reclassified in *Pseudoramibacter alactolyticym* (Clin. Infect. Dis. 1997, Sep.; 25 Suppl. 2: S78-87).

As shown in Table 1, when the primers of SEQ ID NO:1 and SEQ ID NO:2 were used in combination, the DNAs of bacteria of the *Escherichia, Salmonella, Citrobacter, Klebsiella, Enterobacter, Serratia, Hafnia, Plesiomonas, Shigella* and *Yersinia* genera, which are under the Enterobacteriaceae family, and of the *Vibrio, Photobacterium* and *Aeromonas* genera, which are belonged to the Vibrioaceae family, were detected.

When the primers of SEQ ID NO:3 and SEQ ID NO:4 were used in combination, the DNAs of bacteria of the *Staphylococcus, Bacillus* and *Aerococcus* genera were detected.

Thus it is evident that when the primers of SEQ ID NO:1 and SEQ ID NO:2 are used in combination, bacteria of the Enterobacteriaceae and Vibrioaceae families are detected specifically and, when the primers of SEQ ID NO:3 and SEQ ID NO:4 are used in combination, bacteria of the *Staphylococcus, Bacillus* and *Aerococcus* genera are specifically detected.

Example 4

Separation of Bacteria from Foodstuffs by Centrifugation

To steamed noodles (confirmed free of *Staphylococcus aureus*) made from wheat flour, starch, brine and water were added about $4.0 \times 10^4$ cells, per gram of the noodles, of the *Staphylococcus aureus* IFO 3060 strain, 9 times the noodle weight of phosphate buffer (pH 7.2) was added, and the noodles were ground using a Stomachere® homogenizer.

A 1-ml portion of the ground noodle liquid A was centrifuged at 100×g for 1 minute, the supernatant B obtained was centrifuged at 10,000×g for 5 minutes, and the sediment obtained was suspended in 1 ml of brain heart infusion medium (suspension C). The bacterial counts in the ground noodle liquid A, supernatant B and suspension C as measured were $4.1 \times 10^3$/ml, $4.0 \times 10^3$/ml and $4.0 \times 10^3$/ml, respectively. This indicates successful transfer or separation of most of the bacteria initially added to the noodles into the suspension C.

In addition, experiments were carried out in the same manner using strains of the *Escherichia coli* JCM 1649$^T$, *Salmonella typhimurium* IFO 13245, and *Bacillus cereus* IFO 15305$^T$. Similar results were obtained.

Example 5

Detection Limits

<DNA Preparation>
To portions of steamed noodles (confirmed free of *Staphylococcus aureus*) made from wheat flour, starch, brine and water were added about $10^2$, $10^3$, $10^4$ or $10^5$ cells, per gram of the noodles, of the *Staphylococcus aureus* IFO 3960. An amount of 9 times the noodle weight of phosphate buffer (pH 7.2) (cf. Shokuhin no Eiseibiseibutu Kensa (Testing Foods for Health and Microorganisms), published 1983 by Kodansha, page 440) was added to each portion of the noodles, and the noodles were ground using a Stomacher® homogenizer. The bacterial counts in these ground noodle portion were about 10, $10^2$, $10^3$ and $10^4$ per milliliter, respectively.

A 10-ml portion of each ground noodle liquid was centrifuged at 100×g for 2 minute, and the supernatant was centrifuged at 3,000×g for 15 minutes. The sediment was suspended in 5.0 ml of TE buffer (5 mM Tris, 0.1 mM EDTA) for rinsing, the suspension was again centrifuged at 3,000×g for 15 minutes, and the sediment was recovered.

DNA extraction from the sediment was effected using a DNA extraction kit (product of Gentra SYSTEMS), followed by dissolution in 20 µl of TE buffer.

<PCR>
Sterilized water and the buffer solution for PCR were added to 2 µl of each DNA solution obtained in the above manner for adjustment to the following final concentrations: 1.5 mM MgCl$_2$, 50 mM KCl, 10 mM Tris-HCl (pH 8.3), 200 µM dNTPs, 0.2 µM each primer. Thereto was added 1.25 units of Taq DNA polymerase (TaKaRa), and the PCR was carried out with a total liquid amount of 50 µl.

As for the primers, the primer of SEQ ID NO:3 and the primer of SEQ ID NO:4 were used in combination.

As for the temperature conditions for PCR, thermal denaturation was carried out at 94° C. for 30 seconds, annealing at 58° C. for 30 seconds, and DNA elongation at 72° C. for 30 seconds. Under these conditions, the PCR was carried out in 40 cycles. The PCR apparatus used was Geneamp PCR system 9700 (Applied Biosystems).

Each PCR product obtained was electrophoresed on 1.6% agarose gel (TaKaRa) at 100 V for 25 minutes using Mupid-2 (Cosmo Bio), the gel obtained after electrophoresis was stained with ethidium bromide (1.0 µg/ml), and band observation was made under a UV lamp.

Figure 3:
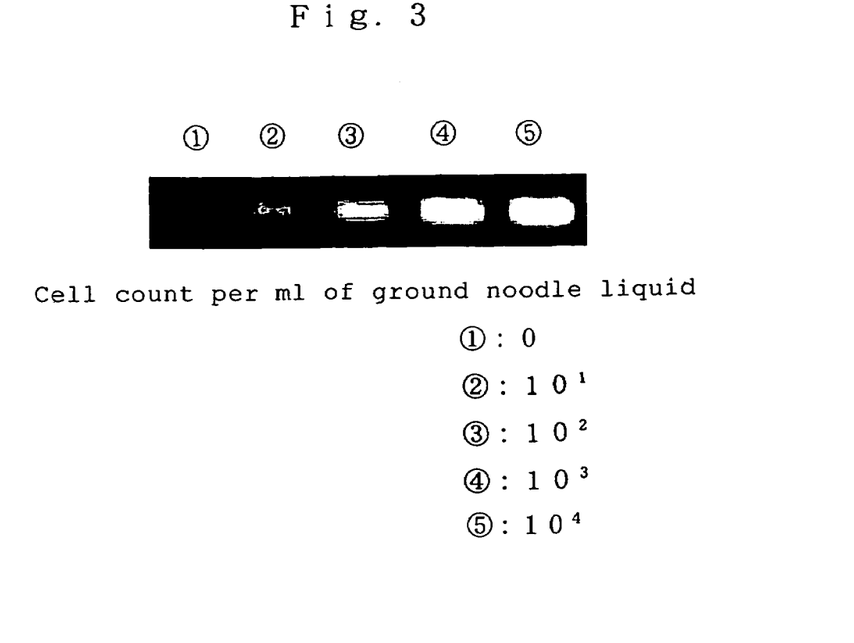
FIG. 3 illustrates the bacterial detection limit in an example of the PCR using the primers of the invention.

The results are shown in FIG. 3. FIG. 3 indicates that when about $10^3$ cells per gram of noodles (about $10^2$ cells per ml of the ground noodle liquid) of *Staphylococcus aureus* are present, the DNA thereof can be detected.

As for the *Escherichia coli* JCM $_{1649}^T$, *Salmonella typhimurium* IFO 13245 and *Bacillus cereus* IFO 15305$^T$ as well, the DNA of each strain could be detected when about $10^3$ bacterial cells per gram of the noodles (about $10^2$ cells per ml of the ground noodle liquid) were present. For *Escherichia coli* and *Salmonella typhimurium*, the primer of SEQ ID NO:1 and the primer of SEQ ID NO:2 were used in combination. For *Bacillus cereus*, the primer of SEQ ID NO:3 and the primer of SEQ ID NO:4 were used in combination.

Example 6

PCR After Cell Growth

<DNA Preparation>

To portions of steamed noodles (confirmed free of *Escherichia coil* or *Bacillus cereus*) made from wheat flour, starch, brine and water were added about 10 cells, per gram of the noodles, of the *Escherichia coil* JCM $1649^T$ or *Bacillus cereus* IFO $15305^T$. An amount of 9 times the noodle weight of brain heart infusion medium was added to each portion of the bacterial cell-added noodles, and the noodles were ground aseptically using a Stomacher® homogenizer.

A 10-ml portion of each ground noodle liquid was cultured at 35° C. for 5-18 hours using a shaking incubator (revolution of 200 rpm). The cell density in the ground noodle liquid before cultivation was 1 cell/ml. In the case of *Escherichia coli*, it was $1.5 \times 10^3$ cells/ml after 5 hours of cultivation, $7.0 \times 10^3$ cells/ml after 6 hours of cultivation, $5.2 \times 10^4$ cells/ml after 7 hours of cultivation, and $2.0 \times 10^9$ cells/ml after 18 hours of cultivation, as a result of bacterial cell proliferation. In the case of *Bacillus cereus*, it was $5.3 \times 10^3$ cells/ml after 5 hours of cultivation, $4.3 \times 10^4$ cells/ml after 6 hours of cultivation, $4.1 \times 10^5$ cells/ml after 7 hours of cultivation, and $7.2 \times 10^8$ cells/ml after 18 hours of cultivation, as a result of cell proliferation.

A 1.3-ml portion of each culture fluid was collected and centrifuged at 100×g for 1 minute, the supernatant was centrifuged at 10,000×g for 5 minutes, and the sediment was recovered. For rinsing, this sediment was suspended in TE buffer (5 mM Tris, 0.1 mM EDTA), the suspension was centrifuged at 10,000×g for 5 minutes, and the sediment was recovered.

To the sediment was added 200 μl of 10% Chelex solution (10% (w/v) Chelex, 10 mM Tris-HCl (pH 8.0), 0.1 mM EDTA), the mixture was heated on a boiling water bath for 5 minutes and then centrifuged at 10,000×g for 5 minutes, and the supernatant was recovered. The supernatant contained DNA, hence was used as the DNA solution for PCR.

<PCR>

Sterilized water and the buffer solution for PCR were added to 1 μl of each DNA solution obtained for adjustment to the following final concentrations: 2.0 mM $MgCl_2$, 50 mM Tris-HCl (pH 8.3), 0.25 mg/ml BSA, 200 μM dNTPs, 0.2 μM each primer. Thereto was added 1.0 unit of Hot Start Taq DNA polymerase (product of Roche Diagnostics), and the PCR was carried out with a total liquid amount of 20 μl.

For *Escherichia coli*, the primers of SEQ ID NO:1 and SEQ ID NO:2 were used in combination. For *Bacillus cereus*, the primers of SEQ ID NO:3 and SEQ ID NO:4 were used in combination.

As for the temperature conditions for PCR, the reaction mixture was maintained at 95° C. for 15 minutes and then thermal denaturation was carried out at 95° C. for 5 seconds, annealing at 59° C. for 10 seconds and DNA elongation at 72° C. for 20 seconds. Under these conditions, the PCR was carried out in 30 cycles. The PCR apparatus used was LightCycler® (product of Roche Diagnostics).

Each PCR product obtained was electrophoresed on 1.6% agarose gel (TaKaRa) at 100 V for 25 minutes using Mupid-2 (Cosmo Bio). The gel obtained after electrophoresis was stained with ethidium bromide (1.0 μg/ml), and band observation was made under a UV lamp.

Figure 4:
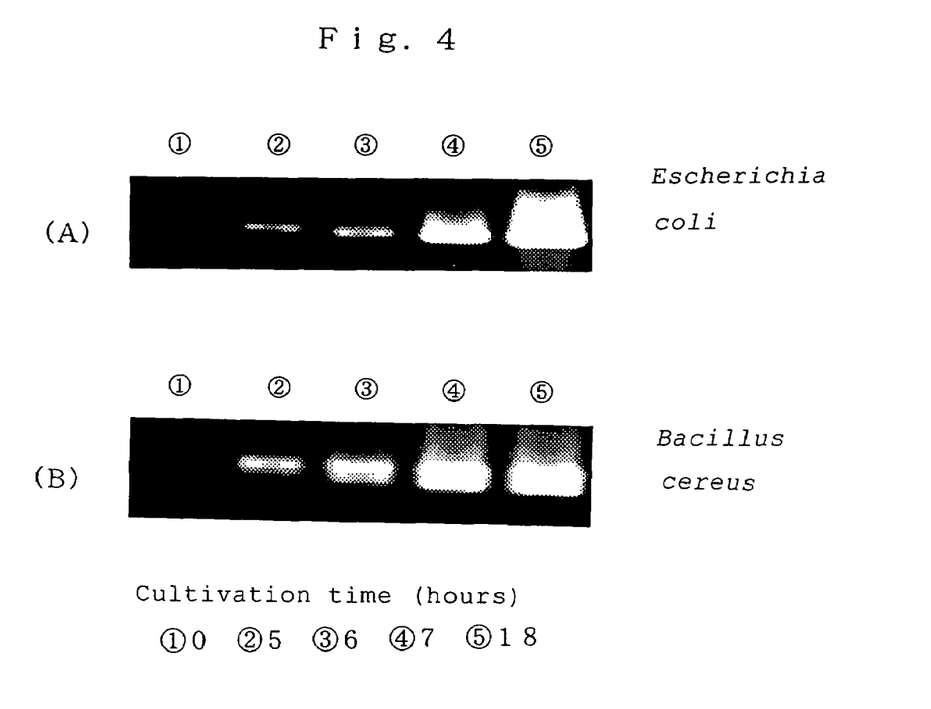
FIG. 4 shows the necessary bacterial cultivation times in other examples of the PCR using the primers of the invention.

The electrophoretic patterns are shown in FIG. 4. (A) in FIG. 4 shows the results with *Escherichia coli*, and (B) in FIG. 4 shows the results with *Bacillus cereus*. In the case of *Escherichia coli*, it is evident, as shown in FIG. 4(A), that when about 10 cells thereof are present in each gram of the noodles, the DNA thereof can be detected by the above PCR after 5 hours or a longer time of cultivation by the above procedure. In the case of *Bacillus cereus*, too, it is evident, as shown in FIG. 4(B), that when about 10 cells thereof are present in each gram of the noodles, the DNA thereof can be detected by the above PCR after 5 hours or a longer time of cultivation by the above procedure.

Further, similar results were obtained with the *Salmonella typhimurium* IFO 13245 strain by the combined use of the primer of SEQ ID NO:1 and the primer of SEQ ID NO:2, and similar results were obtained with the *Staphylococcus aureus* IFO 3060 strain by the combined use of the primer of SEQ ID NO:3 and the primer of SEQ ID NO:4.

INDUSTRIAL APPLICABILITY

The first primer of the invention is a primer for detecting bacteria of the *Escherichia*, *Salmonella* and *Vibrio* genera, and the second primer of the invention is a primer for detecting bacteria of the *Staphylococcus* (in particular *Staphylococcus aureus*) and *Bacillus* (in particular *Bacillus cereus*) genera. Food-derived chloroplasts and mitochondria are not detected by these primers. Therefore, by carrying out the PCR using these primers, it is possible to check the possibility of contamination of foodstuffs by main food poisoning-causing bacteria with ease and high sensitivity.

Therefore, these primers can be suitably utilized in primary screening in testing of foodstuffs relatively low in frequency of contamination for bacteria, in particular in voluntary testing for bacteria by food manufacturers prior to product shipment.

When, in carrying out the method of detecting bacteria according to the invention, the food grinding step and centrifugation procedure are carried out, bacteria are efficiently separated and collected from foodstuffs and, therefore, it is no longer necessary to separate bacteria from foodstuffs and cultivate the same. The testing time is thus shortened accordingly.

The invention claimed is:

1. A primer consisting of the base sequence of base numbers 1 to 30 in SEQ ID NO:1, or a primer which is a DNA comprising at most 40 bases and containing this base sequence on the 3' terminal side thereof.

2. A primer set, comprising:
   the primer of claim 1, and
   a primer consisting of the base sequence of bases 1 to 23 in SEQ ID NO:2, or a primer which is a DNA comprising at most 40 bases and containing this base sequence on the 3' terminal side thereof.

3. A PCR kit, comprising:
   the primer set of claim 2; and
   an additional primer set, comprising
      a primer consisting of the base sequence of base numbers 1 to 24 in SEQ ID NO:3, or a primer which is a DNA comprising at most 40 bases and containing this base sequence on the 3' terminal side thereof and
      a primer consisting of the base sequence of base numbers 1 to 33 in SEQ ID NO:4, or a primer which is a DNA comprising at most 40 bases and containing this base sequence on the 3' terminal side thereof.

4. A method for detecting bacteria which comprises the step i) of extracting DNAs contained in a foodstuff sample to be tested therefrom and the step ii) of carrying out the PCR using a primer set according to claim 2 with the DNA extracted as template and detecting the DNA thus amplified.

5. A primer consisting of the base sequence of base numbers 1 to 24 in SEQ ID NO:3, or a primer which is a DNA comprising at most 40 bases and containing this base sequence on the 3' terminal side thereof.

6. A primer set, comprising:
   the primer of claim 5, and
   a primer consisting of the base sequence of base numbers 1 to 33 in SEQ ID NO:4, or a primer which is a DNA comprising at most 40 bases and containing this base sequence on the 3' terminal side thereof.

7. A method for detecting bacteria which comprises the step i) of extracting DNAs contained in a foodstuff sample to be tested therefrom and the step ii) of carrying out the PCR using a primer set according to claim 6 with the DNA extracted as template and detecting the DNA thus amplified.

8. A primer consisting of the base sequence of base numbers 1 to 33 in SEQ ID NO:4, or a primer which is a DNA comprising at most 40 bases and containing this base sequence on the 3' terminal side thereof.

* * * * *